United States Patent
Najafi

(10) Patent No.: US 10,632,063 B2
(45) Date of Patent: Apr. 28, 2020

(54) COSMETIC KIT

(71) Applicant: PPLUS SKIN CARE LIMITED, Southampton (GB)

(72) Inventor: Mitra Najafi, Southampton (GB)

(73) Assignee: PPLUS SKIN CARE LIMITED, Southampton Hampshire (GB)

( * ) Notice: Subject to any disclaimer, the term of this patent is extended or adjusted under 35 U.S.C. 154(b) by 0 days.

(21) Appl. No.: 15/323,702

(22) PCT Filed: Jun. 12, 2015

(86) PCT No.: PCT/GB2015/051746
§ 371 (c)(1),
(2) Date: Jan. 3, 2017

(87) PCT Pub. No.: WO2016/001624
PCT Pub. Date: Jan. 7, 2016

(65) Prior Publication Data
US 2017/0135950 A1    May 18, 2017

(30) Foreign Application Priority Data
Jul. 3, 2014  (GB) .................................. 1411913.5

(51) Int. Cl.
*A61Q 19/08* (2006.01)
*A61K 8/98* (2006.01)
*A61K 35/16* (2015.01)
*A61K 8/65* (2006.01)

(52) U.S. Cl.
CPC ................ *A61K 8/983* (2013.01); *A61K 8/65* (2013.01); *A61K 35/16* (2013.01); *A61Q 19/08* (2013.01); *A61K 2800/87* (2013.01); *A61K 2800/882* (2013.01); *A61K 2800/91* (2013.01)

(58) Field of Classification Search
None
See application file for complete search history.

(56) References Cited

U.S. PATENT DOCUMENTS

| | | | | |
|---|---|---|---|---|
| 2007/0110737 A1* | 5/2007 | Mishra | ................... | A61K 8/983 |
| | | | | 424/93.72 |
| 2012/0171180 A1* | 7/2012 | Abramson | ............. | A61K 35/16 |
| | | | | 424/93.72 |
| 2013/0114755 A1* | 5/2013 | Cheng | .................. | H04B 7/0854 |
| | | | | 375/295 |
| 2013/0309935 A1* | 11/2013 | Olson | ....................... | A63H 3/20 |
| | | | | 446/330 |
| 2015/0037289 A1* | 2/2015 | Khan | ...................... | A61K 35/35 |
| | | | | 424/93.7 |
| 2016/0206551 A1* | 7/2016 | Boss, Jr. | ................. | A61K 8/983 |

FOREIGN PATENT DOCUMENTS

| | | |
|---|---|---|
| DE | 10 2012 104883 | 12/2013 |
| WO | 2005/065269 | 7/2005 |
| WO | 2006086479 A2 | 8/2006 |
| WO | 2013/007308 | 1/2013 |
| WO | 2013/061309 | 5/2013 |
| WO | WO 2014/126931 * | 8/2014 |

OTHER PUBLICATIONS

Cameli, N. et al. Autologous Pure Platelet Rich Plasma Dermal Injections for Facial Skin Rejuvenation. Dermatologic Surgery 43(6) 826-835, Jun. 2017. (Year: 2017).*
Holme et al. "An Overview of Collection, Processing, Storage and Quality Monitoring of Platelets", Platelet Therapy: Current Status and Future Trends, Jan. 1, 2000 (18 pages).
Fufa et al. "Activation of Platelet-Rich Plasma using Soluble Type I Collagen", Journal of Oral and Maxillofacial Surgery, vol. 66, No. 4, Apr. 1, 2008 (8 pages).
Kim et al., "Can Platelet-Rich Plasma Be Used for Skin Rejuvenation? Evaluation of Effects of Platelet-Rich Plasma on Human Dermal Fibroblast", Annals of Dermatology, vol. 23, No. 4, Jan. 1, 2011 (8 pages).
PCT/GB2015/051746; International Search Report dated Sep. 22, 2015 (14 pages).
GB1411913.5; UK Search Report dated Mar. 9, 2015 (4 pages).

* cited by examiner

*Primary Examiner* — Ralph J Gitomer
(74) *Attorney, Agent, or Firm* — Schwabe, Williamson & Wyatt, P.C.

(57) ABSTRACT

This invention relates to kits that allow the user to apply cosmetic products such as creams and serums to be mixed with a subject's own platelet rich plasma (PRP) and applied to the skin for several days.

6 Claims, 22 Drawing Sheets

Client 2 Group 2

Before

After

Client 3 Group 2

Before

After

Client 1 Group 2

Client 2 Group 1

Client 1 Group 1

Before

After

Client 1 Group 1

Before

After

COSMETIC KIT

CROSS REFERENCE TO RELATED APPLICATION

The present application is a national phase entry under 35 U.S.C. § 371 of International Application No. PCT/GB2015/051746, filed Jun. 12, 2015, entitled "COSMETIC METHODS AND PRODUCTS," which designated, among the various States, the United States of America, and which is hereby incorporated by reference.

This invention relates to methods of improving the appearance of skin or hair. In particular, it relates to cosmetic products such as creams and serums comprising a subject's own platelet rich plasma (PRP), a fraction of plasma which is particularly rich in platelets, and uses thereof. It also relates to uses of cosmetic products, such as creams and serums comprising a subject's own platelet rich plasma in conjunction with treatment to improve the appearance of the skin or hair.

Ageing causes tissue repair and cell regeneration to slow down. Skin ageing is caused by a slowing down of the skin renewal cycles over the years exacerbated by damage to the skin due to stress, photo-exposure, pollution, exposure to cigarette smoke and unhealthy lifestyle factors. The skin aging process is marked by very distinct signs: the appearance of wrinkles, a variation in the skin pigmentation, loss of elasticity and compactness, and the relaxing of the tissues. Skin aging influences the three main skin structures: epidermis, dermal-epidermal junction and dermis. In particular, among the various factors which significantly participate in the skin aging process, is a reduction in the thickness of the dermis. The dermis is a connective tissue having a thickness of 3-4 mm, beneath the epidermis, consisting of a cell population dispersed in an abundant intercellular matrix. The majority of dermal cells are fibroblasts, destined for the synthesis of collagen and elastic fibres. The former have the function of support and resistance, the elastic fibres ensure a correct elasticity of the skin whereas the intercellular matrix in which they are immersed has a strengthening function. As we age the renewal of these important structures slows down and this leads to the signs such as uneven skin tone and wrinkles that many people would like to avoid in order to have a more youthful appearance.

Plasma comprises a multitude of molecules and cells that are responsible for regulating key process involved in tissue repair, including proliferation, chemotaxis. Platelets, initially known to be responsible for blood clotting, release growth factors including Platelet-derived growth factor (PDGF), a potent chemotactic agent, and TGF beta, which stimulates the deposition of extracellular matrix. Both of these growth factors have been shown to play a significant role in the repair and regeneration of connective tissues. The concentrated platelets in PRP deliver an increased number of growth factors to the topical area and activation of the platelets, for example with calcium chloride releases the majority of growth factors from the platelets.

The seven principal known growth factors in platelets are: Platelet Delivered Growth Factors such as (PDGFaa), (PDGFbb), (PDGFab), Transforming Growth Factor beta-, (TGF-b), TGF-b2, Vascular Endothelial Growth Factor (VEGF) and Epithelial Growth Factor As a concentrated source of platelets, plasma contains several cytokines that stimulate tissue regeneration and have an anti-ageing activity. Plasma has received popular attention due to its use in treating sports injuries in professional athletes and it is also known for use in dentistry and wound healing. Plasma therapy, involves centrifuging a person's blood until the blood gets separated in its main compounds: red blood cells, white blood cells and plasma. The richer part of plasma is called PRP or F2 fraction (F2) and the poorer part of plasma is called PPP or F1 fraction (F1). Growth factors can be released by activating the plasma and then injected into the injured tissue.

Plasma, PPP and PRP have been used in a range of applications by injecting it into the skin to reduce the visible signs of ageing and also in medical treatments for wound healing and speeding the repair of damaged tissues. Most medical and cosmetic uses of plasma are done by activating the plasma using calcium chloride to release the growth factors from the platelets and injecting activated plasma into the skin or damaged tissue.

Activated plasma has been injected into the dermal layer of the skin in order to reduce the signs of ageing but this treatment can be painful and lead to redness, soreness and bruising of the skin. The effects of the plasma only last for a few weeks or months and the treatment must be repeated in order to prolong the effect. Various other anti-ageing treatments, such as cosmetic laser treatments are known to have positive effects on the appearance of the skin but also can cause skin irritation, pain and redness in the short term.

It would therefore be advantageous to provide a topical formulation of PRP that could be used to improve the appearance of skin and also can be used after other cosmetic treatments, such as injected PRP and cosmetic laser treatment, to prolong and enhance the effects of the cosmetic treatments so that they could be carried out less frequently.

The object of the present invention is therefore to provide a skin-care product that makes it possible to apply PRP to the skin topically either as a cosmetic treatment alone or after a first cosmetic treatment such as injected PRP treatment or cosmetic laser treatment to prolong and enhance the cosmetic effects of the first cosmetic treatment.

In a first aspect the present invention provides a method of improving the cosmetic appearance of skin and/or hair of a subject wherein the method comprises,
(a) Providing a sample of PRP from the subject;
(b) Providing a cosmetically acceptable carrier;
(c) Admixing a portion of the PRP to a portion of the cosmetically acceptable carrier to form a topical composition;
(d) Applying the topical composition to an area of the subject's skin.
(e) Repeating steps (c) and (d)

Steps c and d may be repeated every day for up to 8 days. After 8 days fresh PRP may be provided from the subject to continue the treatment. An advantage of the present method is that a portion of PRP may be mixed with activator each day immediately before it is applied to the skin. This means that growth factors are kept inside the platelets, which protects them from degradation, until the activator is mixed with PRP. The growth factors are then released from the platelets into the composition. The advantage of this method is that it allows the treatment to be used every day with fresh growth factors that have just been released from the platelets immediately before application to the skin. These advantages are provided without having to provide a new sample of PRP from the subject each day. Therefore, the subject can continue the treatment at home for 8 days using freshly activated PRP every day.

Various authors have discussed the use of a patient's own plasma in wound healing and in cosmetic procedures and there is varied and inconsistent use of a number of terms in this field. In this application the terms PRP and F2 are used to describe the richer fraction of plasma that contains a higher number of platelets and the terms PPP and F1 are used to describe the poorer fraction of the plasma that contains a lower number of platelets. This is shown in FIGS. 27-29. The methods described herein may, preferably be performed using the PRP fraction of plasma. This is advantageous because the higher number of platelets provides a richer source of growth factors and skin enhancing factors.

In contrast to the use in this application, other authors have used the term PRP to describe the whole plasma fraction of the blood rather than just the fraction of plasma that is rich in platelets.

An activator may be admixed with the PRP within less than 4 hours, within less than 3 hours, within less than 2 hours, within less than 1 hour, within less than 30 minutes, within less than 20 minutes, within less than 10 minutes or within less than 8 minutes before the topical composition is applied to the subject's skin.

Preferably an activator may be admixed with PRP immediately before the topical composition is applied to the skin. Immediately before means a few minutes or seconds before, for example, immediately before may mean the PRP is admixed with an activator less than 5 minutes, less than 2 minutes, less than one minute or less than 30 seconds before applying the mixture to the skin. This is advantageous because platelets in the PRP may be activated and release growth factors immediately before applying the composition to the skin so that the growth factors do not degrade before they are applied to the skin and there may be a high level of growth factors in the composition.

The cosmetically acceptable carrier may comprise an activator and the topical composition may be applied to the area of the subject's skin immediately after admixing the cosmetically acceptable carrier comprising activator with the PRP.

The topical composition may be applied to the area of the subject's skin within less than 4 hours, within less than 3 hours, within less than 2 hours, within less than 1 hour, within less than 30 minutes, within less than 20 minutes, within less than 10 minutes or within less than 8 minutes of the activator mixing with the PRP.

Preferably the cosmetically acceptable carrier may be admixed with PRP immediately before the topical composition is applied to the skin. Immediately before means a few minutes or seconds before, for example, immediately before may mean the PRP is admixed with the cosmetically acceptable carrier less than 5 minutes, less than 2 minutes, less than one minute or less than 30 seconds before applying the mixture to the skin. This is advantageous because platelets in the PRP may be activated and release growth factors immediately before applying the composition to the skin so that the growth factors do not degrade before they are applied to the skin and there may be a high level of growth factors in the composition.

The PRP may be stored separately from the cosmetically acceptable carrier comprising an activator and the PRP may be mixed with the cosmetically acceptable carrier comprising an activator immediately before applying the composition to the skin.

In some embodiments the cosmetically acceptable carrier may not comprise an activator and an activator may be admixed with the PRP and the cosmetically acceptable carrier immediately before application of the mixture to the skin.

If the activator is not in the cosmetically acceptable carrier the PRP may be mixed with the cosmetically acceptable carrier soon after it is made and stored as a composition comprising PRP and the cosmetically acceptable carrier. This is advantageous because the cosmetically acceptable carrier may comprise ingredients that stabilise or preserve the PRP and/or platelets in the PRP. An activator may be stored separately from the composition comprising the cosmetically acceptable carrier and PRP. The activator may be admixed with the composition immediately before applying the composition to the skin.

Step (e) or steps (c) and (d) may be repeated at least once a day, at least twice a day, at least three times a day, at least four times a day or at least six times a day.

Step (e) or steps (c) and (d) may be repeated for at least two days, at least three days, at least four days, at least five days, at least six days, at least seven days, at least eight days, at least nine days or at least ten days.

Step (e) may be repeated at least once a day for at least eight days.

The activator may be collagen. This is advantageous because collagen is naturally occurring in the skin and therefore is not likely to cause adverse reactions in the skin. The activator may not be calcium chloride. This is advantageous because calcium chloride can cause adverse reactions and/or be irritating to the skin.

The method may be performed on an area of the subject's skin that has been treated using PRP injection or another cosmetic treatment such as cosmetic laser skin treatments.

The method may comprise, before or after step (c), a further step (f) injecting a portion of the platelet rich plasma into one or more areas of the subject's skin. When the method is used in conjunction with injecting PRP into an area of the subject's skin the topical composition is applied to at least the same area of the subject's skin. When the method is used in conjunction with injecting PRP into an area of the subject's skin the topical composition may be applied to at least the same area of the subject's skin immediately after or within an hour after the injections have been performed and then the topical composition may be applied to the same area of skin repeatedly thereafter.

According to a further aspect of the invention we provide a method for improving the appearance of the skin and/or hair of a subject comprising the steps of:

(g) Providing a sample of platelet rich plasma from the subject;
(h) Injecting a first portion of platelet rich plasma into one or more areas of the subject's skin;
(i) Combining a second portion of platelet rich plasma with a cosmetically acceptable carrier to provide a topical composition;
(j) Applying the topical composition from step (i) to the one or more areas of the subject's skin where the platelet rich plasma was injected in step (h).

Platelet rich plasma may be provided by centrifuging a sample of blood from a person in order to separate the platelets from the other blood cells and taking a fraction comprising plasma with a high concentration of platelets.

The PRP may comprise more than 10,000 platelets/$\mu$l, more than 10,000 platelets/$\mu$l, more than 10,000 platelets/$\mu$l, more than 10,000 platelets/$\mu$l, more than 10,000 platelets/$\mu$l, more than 100,000 platelets/$\mu$l, more than 500,000 platelets/$\mu$l or more than 900,000 platelets/$\mu$l. The PRP may comprise Platelet Delivered Growth Factors such as (PDGFaa), (PDGFbb), (PDGFab), Transforming Growth Factor beta-, (TGF-b), TGF-b2, Vascular Endothelial Growth Factor (VEGF) and Epithelial Growth Factor (EGF).

The PRP may be autologous, i.e. taken from a subject and injected back into the same subject. This is advantageous because it avoids any risk of disease transmission between a donor and recipient and also avoids the possibility of reactions to foreign tissues or different ABO blood antigens. It also avoids allergic or adverse reactions.

The area of skin where the topical composition is applied may be on any part of the body. In particular the area of skin where the topical composition is applied may be on the face, scalp, neck, chest, hands, arms, legs, abdomen or buttocks. It is advantageous to apply the topical composition to areas where ageing skin causes concern such as the face and neck. It is also advantageous to apply the topical composition to the scalp because it can prolong the life of hair follicles and increase hair growth. For use on the scalp the topical composition may be hair Gel, hair lotion or leave in conditioner. The topical composition may be formulated for use after PRP injection into the scalp. The topical composition may be formulated for use with other hair-restoring treatments.

The portion of the platelet rich plasma that is injected into the skin may be activated by mixing it with activating agents such as calcium chloride or collagen before injection into the skin. Adding calcium chloride or collagen to the PRP causes the platelets to release most of the growth factors very quickly. This is advantageous because it provides a high concentration of growth factors in the area where the PRP is injected.

The portion of PRP that is reserved for admixing with the cosmetically acceptable carrier may have an activator such as calcium chloride or collagen added to it.

The activator may be collagen. This is advantageous because collagen is naturally occurring in the skin and therefore is not likely to cause adverse reactions in the skin. The activator may not be calcium chloride. This is advantageous because calcium chloride can cause adverse reactions and/or be irritating to the skin.

The portion of PRP that is reserved for admixing with the cosmetically acceptable carrier may have no activator added to it. This is advantageous because calcium chloride can be irritating to the skin. This is further advantageous because the growth factors are preserved inside the platelets until the platelets are activated.

Portions of PRP without activator may be added to a cosmetically acceptable carrier that comprises an activator shortly before being applied to the skin, for example before being applied to the skin. It is advantageous to addmix a portion of PRP without activator and a portion of a cosmetically acceptable carrier that comprises activator immediately before applying the mixture to the skin. For example they may be mixed a few seconds to or up to two minutes before applying to the skin. This ensures that the growth factors are released from the platelets just before the cosmetic composition is applied to the skin so that the growth factors are as active as possible when they are applied to the skin. The PRP may be stored without an activator for several days, for example at least 2 days, at least three days, at least four days, at least five days, at least six days, at least seven days, at least eight days, at least nine days at least ten days or at least two weeks and then added to the cosmetically acceptable carrier comprising an activator which makes platelets release growth factors quickly after mixing. PRP may be stored at room temperature, for example at about 22° C. PRP may not be stored in a refrigerator (for example at about 4° C. because cold storage will activate platelets during storage rather than when mixed with an activator. PRP may also be stored frozen but the platelets are damaged by freezing and release the growth factors shortly after the PRP is thawed. If freezing is used the PRP may be frozen in portions and each portion may be thawed immediately before application to the skin to avoid degradation of the growth factors. PRP may be stored for several weeks or several months frozen. When frozen PRP is thawed it may be mixed with the cosmetically acceptable carrier and applied to skin immediately because growth factors may be released from the platelets as the thawing process may act as an activator.

The cosmetically acceptable carrier may comprise an activator. The cosmetically acceptable carrier may comprise calcium chloride. The cosmetically acceptable carrier may comprise collagen. The cosmetically acceptable carrier may comprise an activator such as collagen, soluble collagen, or hydrolyzed collagen that is less likely than calcium chloride to irritate the skin or cause adverse reactions. Collagen is present in the skin and therefore provides a more natural activator than calcium chloride. Collagen may act as a gentler activator causing growth factors to be released from the platelets at a slower rate than calcium chloride does. It is therefore suitable for use in the cosmetically acceptable carrier of the present invention. The topical composition may comprise an activator that is not calcium chloride.

The activator may be collagen, soluble collagen or hydrolysed collagen and may be from any source such as animal collagen, bovine collagen or synthetic collagen.

Advantageously, the cosmetically acceptable carrier may comprise an activator and be stored separately from the PRP. A portion of cosmetically acceptable carrier may be mixed with a portion of PRP within 1 hour, within 30 minutes, within 20 minutes or within 10 minutes before the composition is applied to the skin. Preferably a portion of cosmetically acceptable carrier may be mixed with a portion of PRP and applied to the skin immediately or within a few seconds up to 2 minutes of mixing. Where the cosmetically acceptable carrier comprises an activator the activator may be calcium chloride or collagen. Collagen may be an advantageous activator for inclusion in a cosmetically acceptable carrier because it may not cause irritation of the skin.

Each portion of PRP and cosmetically acceptable carrier may be just enough for one application. This is advantageous because just enough PRP and cosmetically acceptable carrier may be mixed for one application and the mixture applied to the skin immediately, for example within a few seconds or up to two minutes. This means that the growth factors are released from PRP immediately before application to the skin so that they are fresh and active when they are applied to the skin. The portions of PRP and cosmetically acceptable carrier may be roughly equal in volume so that it is simple to make a 1:1 mixture of the two components.

The cosmetically acceptable carrier may comprise or consist of a cream, gel, serum, balm, sun cream, after sun cream, foundation, tinted cream, tinted sun cream, soothing anti redness cream with green tint, scalp serum. solution, suspension, emulsion, ointment, foam, paste, lotion, powder, soap, surfactant-containing cleansing oil or spray.

The cosmetically acceptable carrier may advantageously be a cream, gel, lotion or a serum.

The cosmetically acceptable carrier may comprise at least one ingredient to increase penetration of the platelet rich plasma into the skin. A composition that comprises at least one ingredient that increases penetration into the skin may be a serum. A serum may also have a consistency, lipid content and/or hydrophobicity that increases the amount of penetration into the skin.

The cosmetically acceptable carrier may comprise or consist of a dressing, adhesive bandage, gauze, or a facial mask. PRP may be soaked into a facial mask that is applied to the skin after PRP has been injected. This can reduce irritation, swelling, pain and redness of the skin at the site where the PRP has been injected.

The cosmetically acceptable carrier may comprise the ingredients from table 4 and at least one preservative from table 5.

The carrier may comprise at least one humectant, at least one emollient and at least one emulsifier.

The cosmetically acceptable carrier may be suitable for preserving and stabilising platelet rich plasma that is not mixed with calcium chloride or collagen.

The cosmetically acceptable carrier may not comprise an activator. The cosmetically acceptable carrier may not comprise calcium chloride. The cosmetically acceptable carrier may comprise an activator.

The cosmetically acceptable carrier may comprise a suitable amount of collagen to act as an activator of platelets.

The cosmetically acceptable carrier may not comprise calcium chloride. The cosmetically acceptable carrier may not comprise any activator except for collagen.

The cosmetically acceptable carrier may comprise at least one ingredient to increase penetration of the platelet rich plasma or growth factors into the skin.

The cosmetically acceptable carrier may further comprise one or more ingredients from table 1 or table 2.

The cosmetically acceptable carrier may further comprise one or more ingredients selected from monocytes, stem cells, gene therapy products, vitamins, palmitate retinol, tocoferil acetate, sodium ascorbil phosphate, D-panthenol, peptides, recombinant growth factors, micronized human-identical hormones, aminoacids, phyto-extracts, anti-oxidants, lipoic acid, DMAE, collagen, GAG, hyaluronic acid, proteoglycans, adenine, guanine, cytosine, thimine, trace elements, minerals, proteases, ceramides, polisaccarides, algae and marine extracts.

In another aspect the present invention provides a cosmetic composition comprising the cosmetically acceptable carrier and platelet rich plasma. Between 10 and 20 ml of PRP may be diluted with cosmetic composition up to a final volume of 50 ml.

The platelet-rich plasma concentration in the cosmetic composition may between 0.1 and 50% (w/w), between 1 and 50%, between 2 and 30%, between 4 and 10% or between 30 and 50% of the total weight of the composition.

The PRP may have no activator added. The cosmetically acceptable carrier may comprise no activator. The cosmetic composition may comprise no activator.

The cosmetic composition may comprise active growth factors for at least 1 day, at least 2 days, at least 3 days, at least 4 days, at least 5 days, at least 6 days, at least 7 days, at least 10 days, at least 2 weeks or at least 3 weeks.

In the method of the present invention the step of applying the cosmetic composition to the area of skin where PRP has been injected may be repeated at least twice, at least three times, at least four times, at least five times, at least six times, at least seven times, at least eight times or at least nine times.

In the method of the present invention the step of applying the cosmetic composition to the area of skin where PRP has been injected may be repeated at least once every day, at least twice daily, at least three times daily, at least four times daily. The step of applying the cosmetic composition to the area of skin where the PRP has been injected may be repeated once or twice daily for up to 8 days.

In the method of the present invention the step of applying the cosmetic composition to the area of skin may be repeated for at least two days, at least three days, at least four days, at least six days, at least seven days, at least 10 days, at least two weeks, at least three weeks, at least four weeks, at least six weeks or at least 8 weeks.

This is advantageous because, after the PRP injection treatment, applying the cosmetic composition comprising PRP may reduce immediate soreness, redness, swelling or bruising. This is also advantageous because, after PRP injection treatment, applying the cosmetic composition comprising PRP may prolong and/or enhance the cosmetic effect of the PRP injection treatment.

In a further aspect, the present invention provides a kit suitable for use in performing the method of the present invention.

The kit may comprise one or more containers comprising chambers suitable for storing PRP for one or more days. The one or more containers may be sterile. The one or more chambers may be arranged to allow the PRP to be introduced into the container under sterile conditions. The Kit may comprise one or more portions of cosmetically acceptable carrier. The kit may be arranged to allow mixing of a portion the PRP from the PRP container with a portion of the cosmetically acceptable carrier. The kit may be arranged so that a portion of PRP and a portion of cosmetically acceptable carrier can be mixed to provide a PRP composition and the composition can be applied to the skin.

This is advantageous because the cosmetically acceptable carrier may comprise an activator. When a portion of PRP and a portion of cosmetically acceptable carrier are mixed the platelets in that portion of PRP may be activated and release growth factors. The remainder of the PRP in the container may remain un-activated and may preserve the growth factors it contains. Freshly activated PRP may therefore be applied every day for several days.

The kit may comprise a suitable container for storing PRP, one or more portions of the cosmetically acceptable carrier comprising collagen as an activator and instructions for use. The user may then admix a portion of PRP with a portion of cosmetically acceptable carrier immediately before applying the mixture to the skin. The container for storing PRP may be designed to exclude airflow into the container. The container for storing PRP may be sterile inside.

For example, the kit may comprise 8 ampules each containing a portion of cosmetically acceptable carrier including collagen, a container for the PRP and instructions for use.

The kit may further comprise a mini vibration table/Agitator and the instruction for use.

An agitator may be advantageous because it is advantageous to store the PRP with agitation to prolong the life of the platelets. Platelets that have been stored with agitation have a greater amount of growth factors on day 8 than platelets that have not been stored with agitation. The kit may also be adapted for storage at room temperature as storage at room temperature improves the storage time of the platelets and means that there are more growth factors on day 8 of storage.

The kit may further comprise instructions for use. The instructions for use may be use in a method of the present invention.

The container may be sterile. The container may be arranged to allow oxygen penetration into the container. The container may be arranged not to allow oxygen penetration into the container. The kit may comprise a container according to the present invention comprising a cosmetically acceptable carrier in at least one chamber and at least one chamber arranged to accept a portion of PRP. The kit may further comprise suitable equipment for drawing blood, suitable containers for holding blood while it is centrifuged, suitable equipment for removing a PRP fraction from the blood and/or suitable equipment for injecting PRP into the skin.

In another aspect the present invention provides a container comprising a first chamber and a second chamber arranged so that contents of the first chamber and contents of the second chamber are mixed as they exit the container. The container may be sterile. A cosmetically acceptable carrier contained in the first chamber and the second chamber is arranged to accept platelet rich plasma. The container may be sterile. A portion of PRP may be put into the second chamber of the container. The PRP may be stored in the second chamber of the container until the user is ready to apply the cosmetic composition. When the container is used a portion of the cosmetically acceptable carrier in the first chamber and a portion of the PRP in the second chamber leave the container and are mixed as they leave the container to provide a cosmetic composition comprising the cosmetically acceptable carrier and PRP. The cosmetically acceptable carrier and the PRP may be mixed in suitable proportions to provide a cosmetic composition of the invention.

The cosmetically acceptable carrier may be contained in a first chamber of the container and PRP may be contained in a second chamber of the container. This is advantageous because the carrier may comprise an activator, for example calcium chloride, collagen or another activator. The PRP may remain in a chamber of the container and not be activated for several days so growth factors remain inside the platelets in the PRP. When the cosmetic composition is required the container may be activated and carrier may be mixed with PRP. The platelets in the PRP may release growth factors when they are mixed with the carrier that comprises an activator and therefore the resulting cosmetic composition may comprise a high level of active growth factors. This arrangement is advantageous because the growth factors may remain active inside the platelets for several days before being released when the PRP is mixed with a carrier comprising an activator. The container may be arranged so that a portion of the PRP and a portion of the carrier may be released at each use of the container. PRP may be prepared once at the time that blood is taken from a subject and put into one chamber of the container. The PRP can thereby be stored without activation until needed and only a portion of the stored PRP may be mixed with carrier including activator each day before applying the composition to the skin.

The cosmetically acceptable carrier that does not comprise an activator may be contained in a first chamber of the container and PRP may be added to the cosmetically acceptable carrier. An activator may be contained in a second chamber of the container. This is advantageous because the carrier may comprise ingredients that stabilise PRP and/or stabilise growth factors inside the platelets in the PRP. An activator, for example calcium chloride, collagen or another activator may be contained in a second chamber of the container. The PRP and cosmetically acceptable carrier may remain in a chamber of the container and the PRP may not be activated for several days so growth factors remain inside the platelets in the PRP. When the cosmetic composition is required the container may be activated and the activator may be mixed with cosmetically acceptable carrier and PRP. The platelets in the PRP may release growth factors when they are mixed with the activator and therefore the resulting cosmetic composition may comprise a high level of active growth factors. This arrangement is advantageous because the growth factors may remain active inside the platelets for several days before being released when the PRP is mixed with an activator. It is also advantageous because the PRP is mixed with a cosmetically acceptable carrier soon after it is made and the cosmetically acceptable carrier can stabilise and preserve the PRP until it is mixed with an activator. The container may be arranged so that a portion of the PRP mixed with cosmetically acceptable carrier and a portion of the activator may be released at each use of the container. PRP may be prepared once at the time that blood is taken from a subject and put into one chamber of the container with the cosmetically acceptable carrier. The PRP can thereby be stored without activation until needed and only a portion of the stored PRP may be mixed with activator each day before applying the composition to the skin.

In order to prolong the life of the platelets and preserve the growth factors inside them it is advantageous to store the PRP at room temperature. It is also advantageous to store the PRP so that it is agitated. It is further advantageous to store the PRP with low oxygen and minimal airflow. It is further advantageous to mix an activator with the PRP immediately before applying the mixture to the skin so that the growth factors are released from the platelets immediately before the mixture is applied to the skin. The kit is arranged to provide all of these features by providing a storage container for the PRP that is airtight and sterile, providing a device for agitating the PRP in the container during storage. The container may be suitable for storage at room temperature. The activator may be included in the cosmetically acceptable composition so that it can be mixed with the PRP immediately before applying to the skin.

There now follows by way of example only a detailed description of the present invention with reference to the accompanying drawings, in which.

FIG. 4 shows pictures of the treated areas of patients 1, 2 and 3 from group 1 and patients 1, 2 and 3 from group 2 showing a comparison of the skin before the treatment and after the treatment. Group 1 had PRP injections in the treated area followed by using serum mixed with PRP each day for 16 days. Group 2—only used serum mixed with PRP each day for 24 days on one side of their face (fresh blood was taken every 8 days) Group 3—used the collagen serum only (without adding PRP to it).

Figure 5:
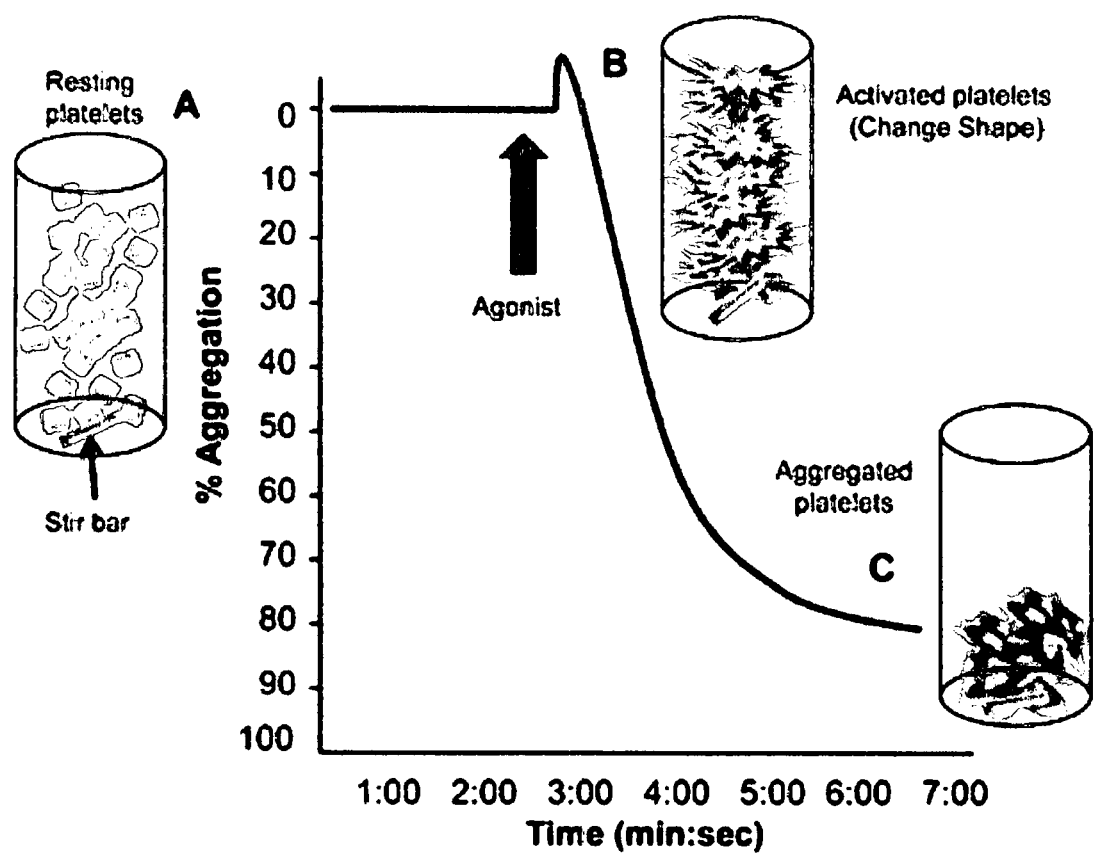

FIG. 5 shows Light transmittance platelet aggregometry. The aggregometer measures changes in light transmission of a stirred platelet suspension exposed to a platelet agonist. It is calibrated by a cuvette containing platelet poor plasma which equates to 100% light transmission. Platelet rich plasma stirred in the absence of platelet agonist equates to 0% light transmission (baseline, A). Change in platelet shape due to platelet activation induced by addition of a platelet agonist results in a short decrease in the light transmission (B). When platelet aggregates are forming an increase in the light transmission is recorded by the device and calculated as percentage of aggregation (C).

Figure 6:
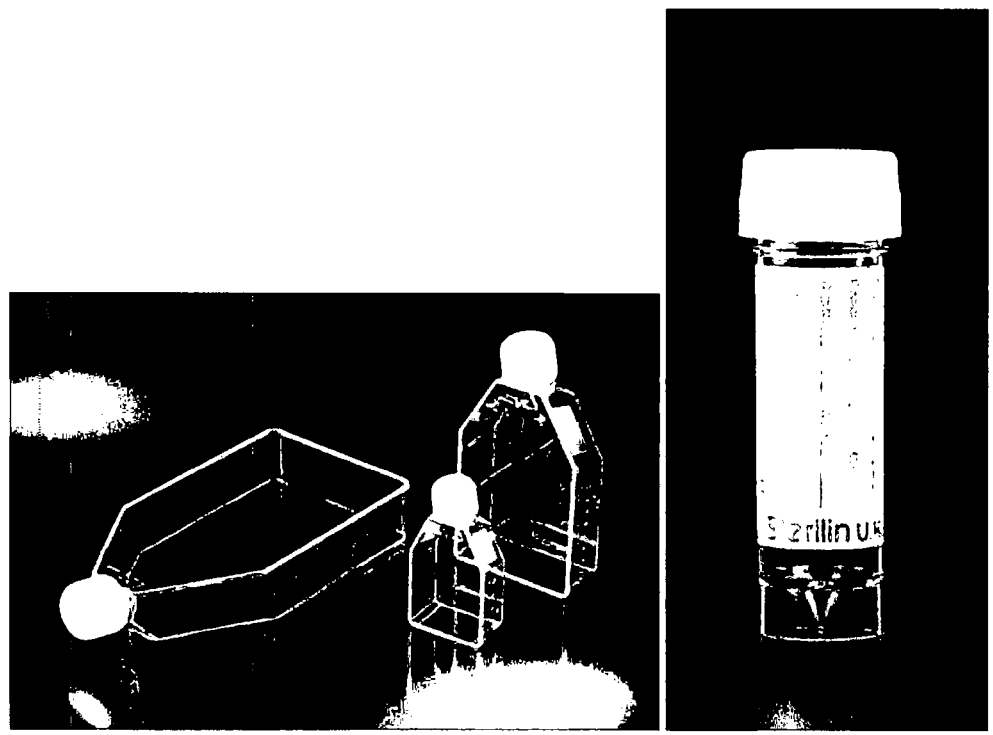
Figure 7:
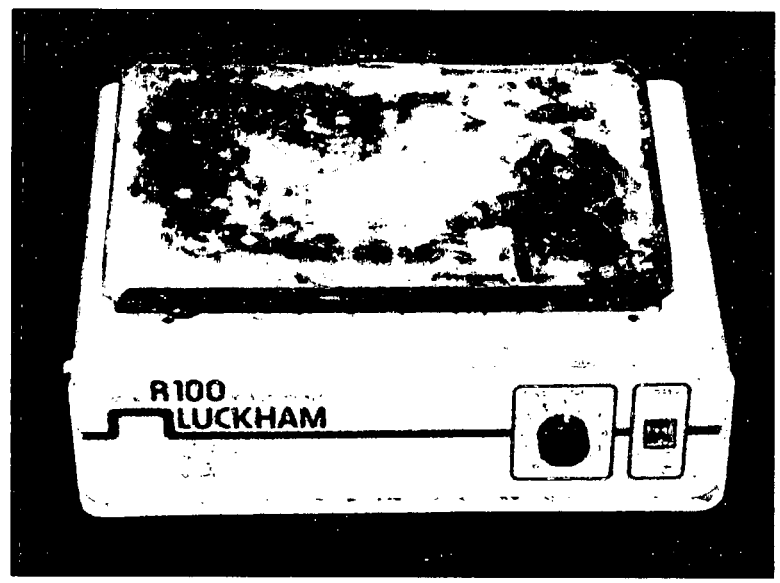
Figure 8:
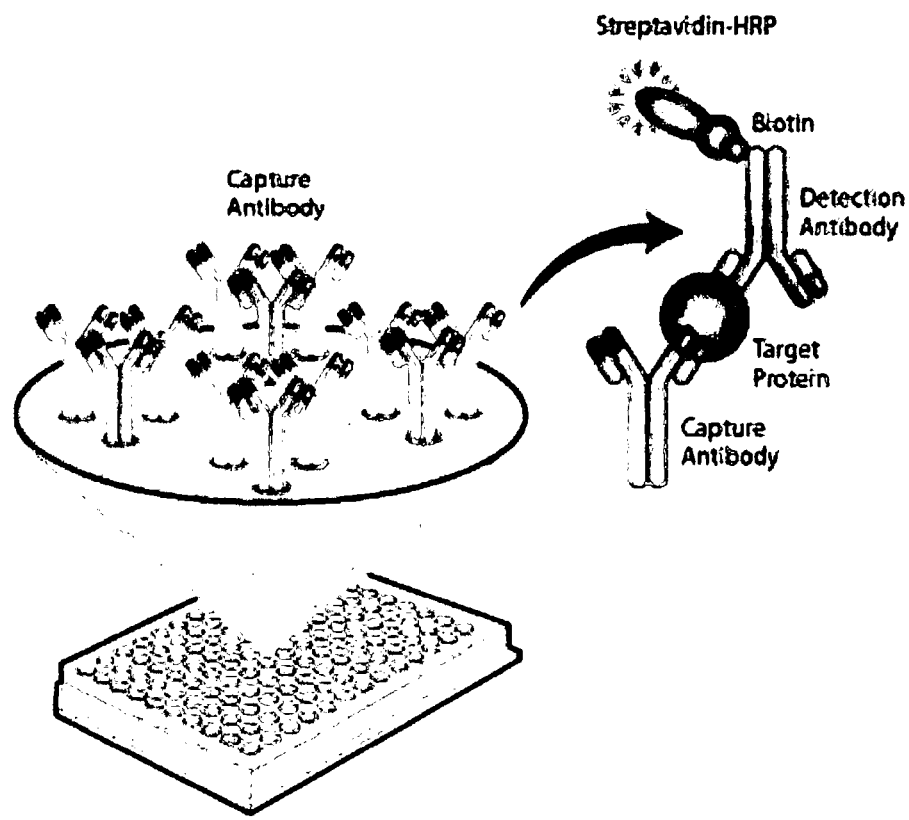

FIG. 6 shows the PRP storage containers: (a) 70 mL Nunc™ flask (smallest shown) (b) 30 mL Sterilin™ universal, FIG. 7 shows Luckham R100 Rotatest Shaker FIG. 8 shows the ELISA plate is provided already coated with a capture antibody directed against human PDGF-BB.

Figure 9:
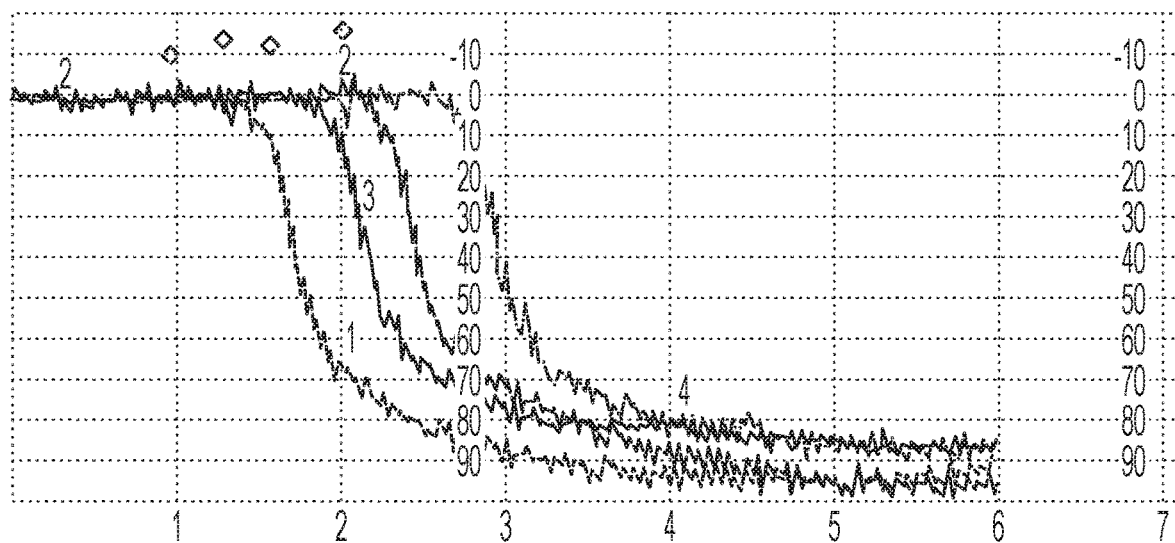
Figure 10:
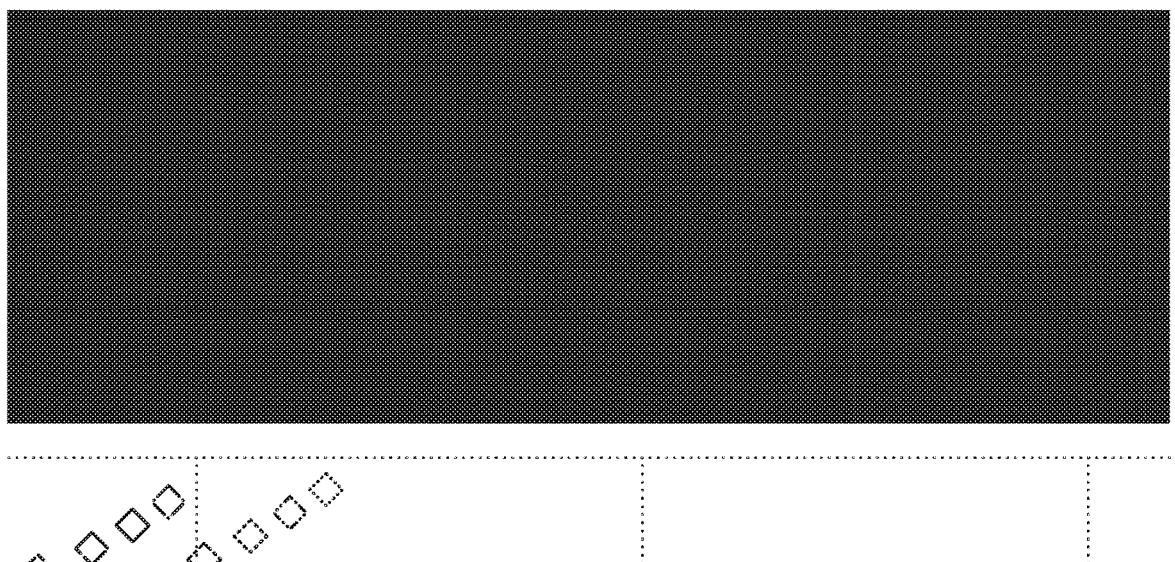
Figure 11:
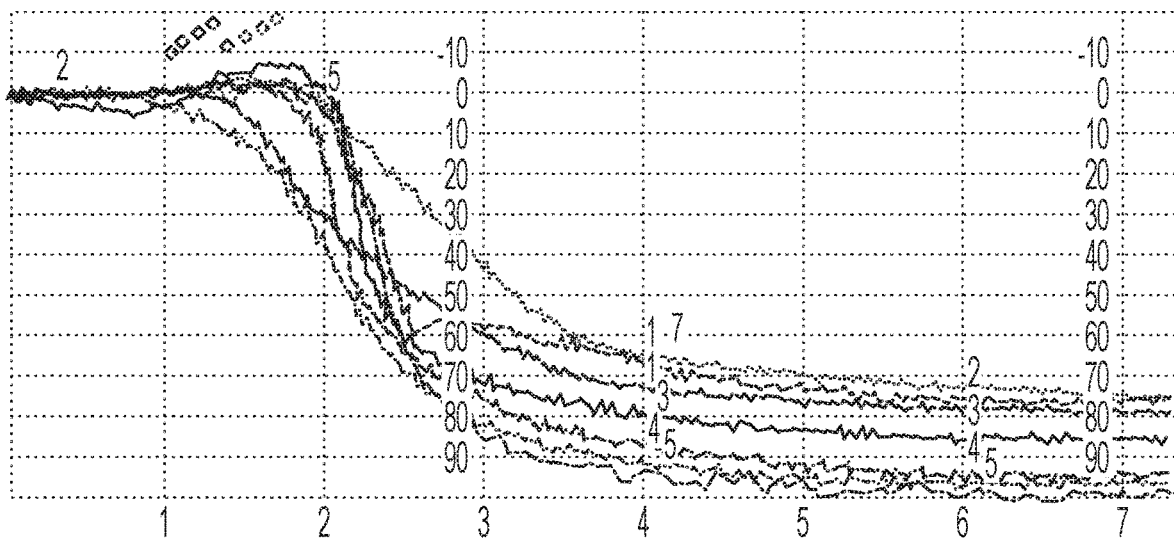
Figure 12:
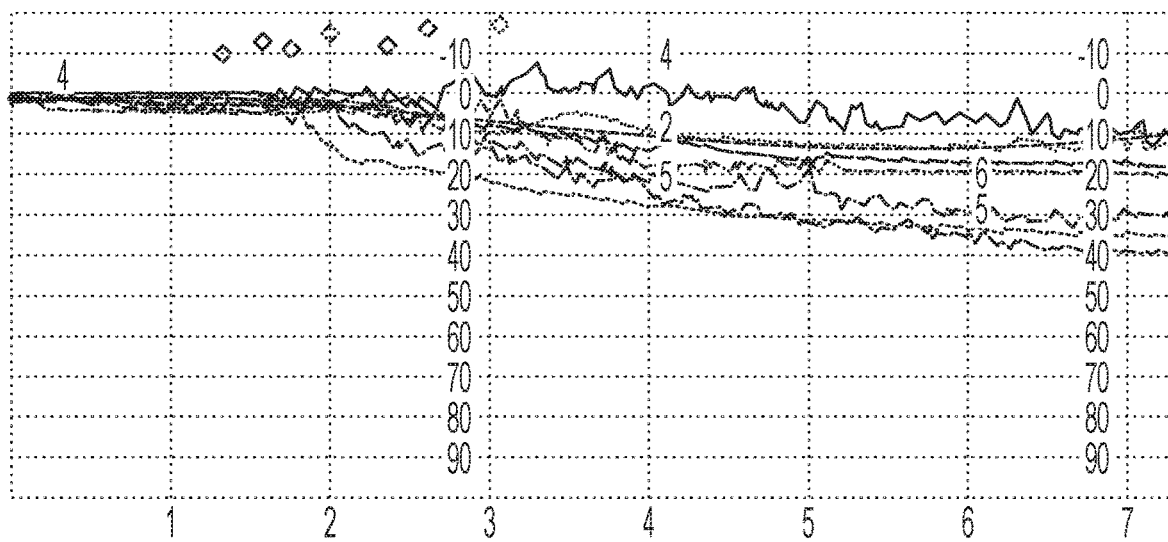
Figure 13:
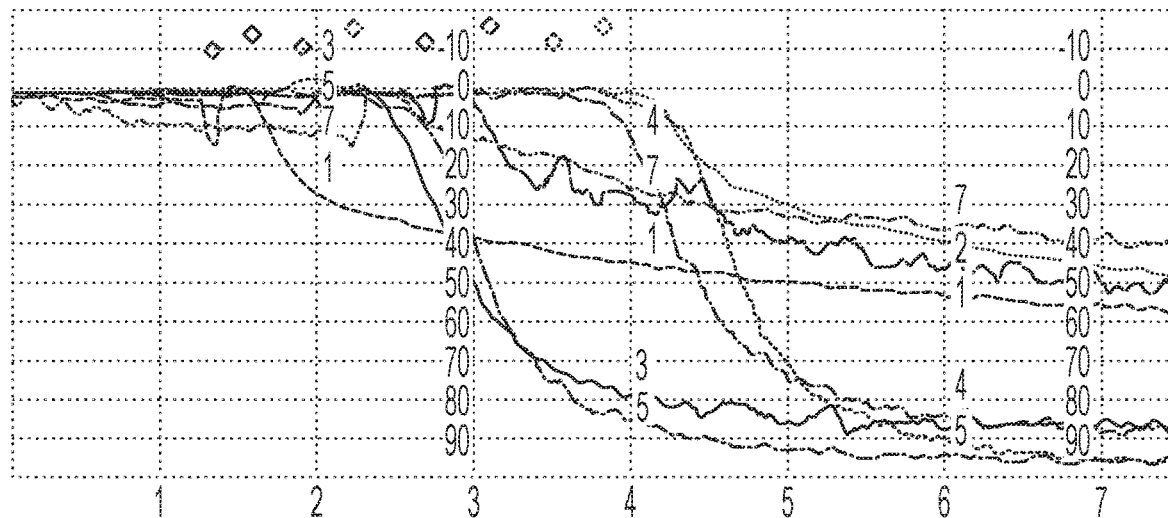
Figure 14:
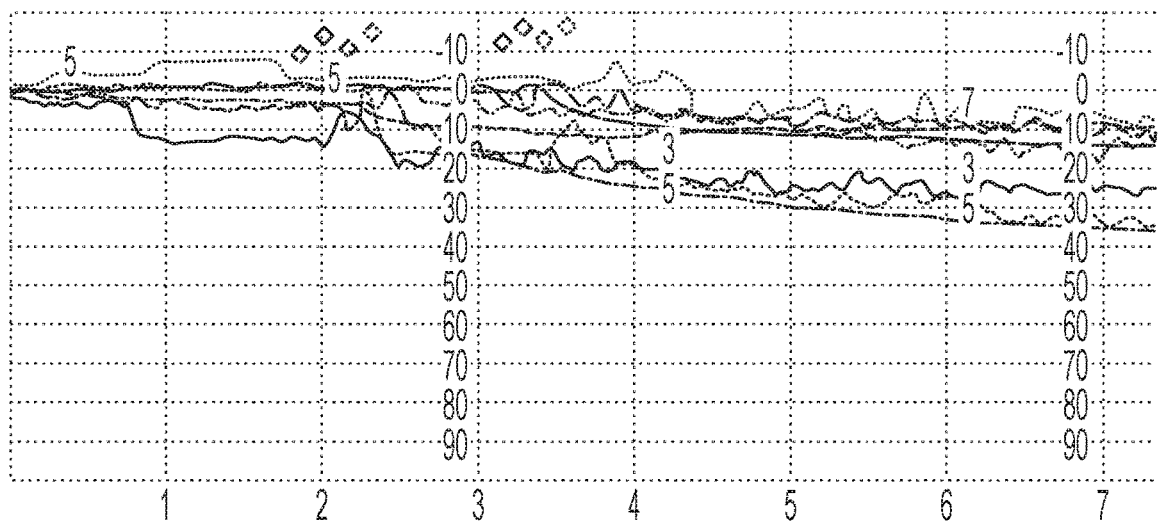
Figure 15:
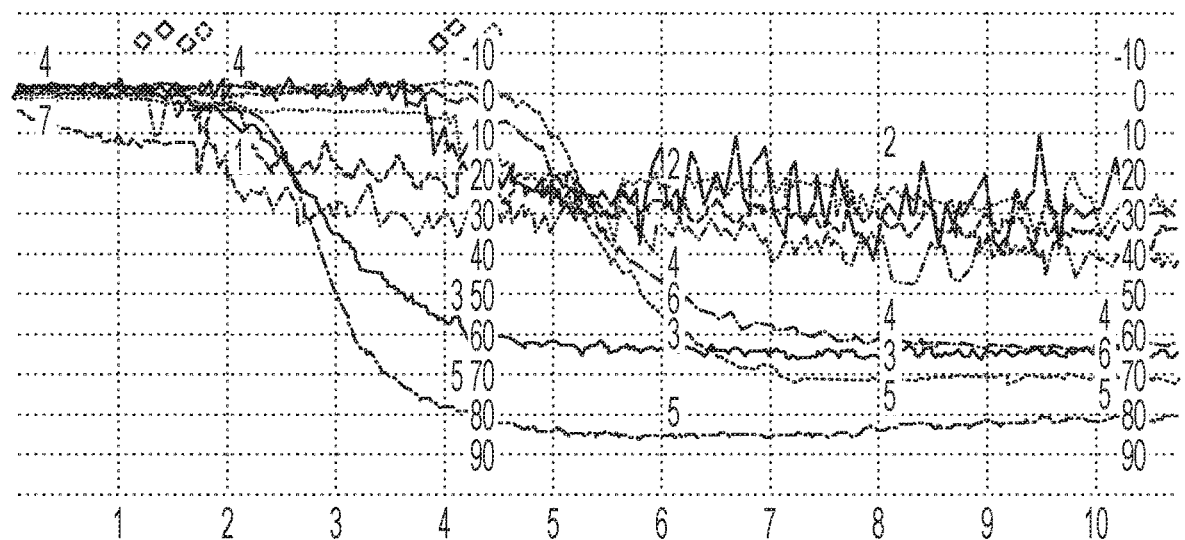
Figure 16:
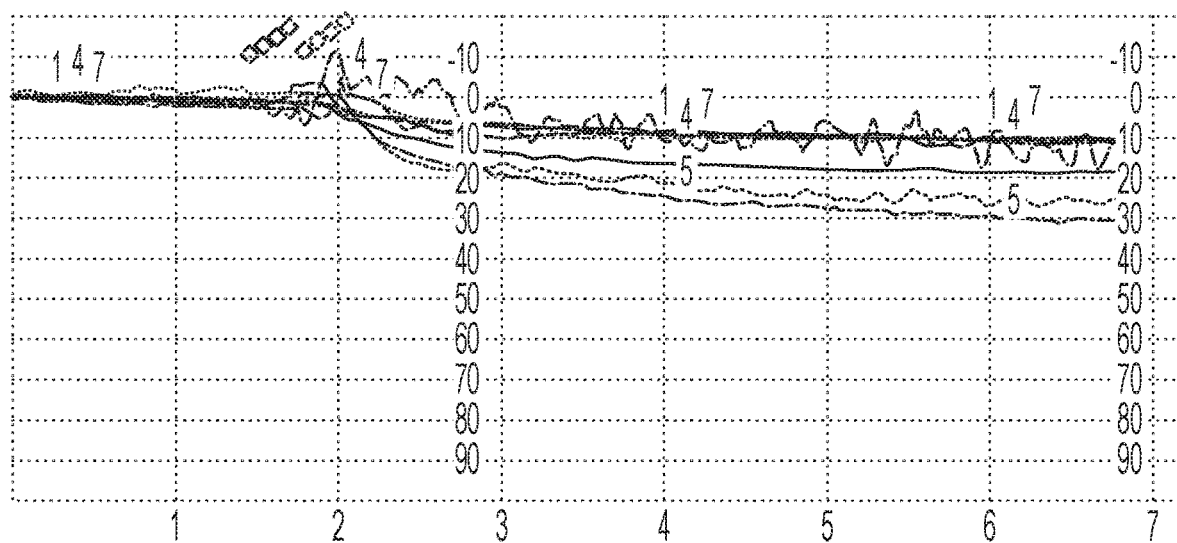
Figure 17:
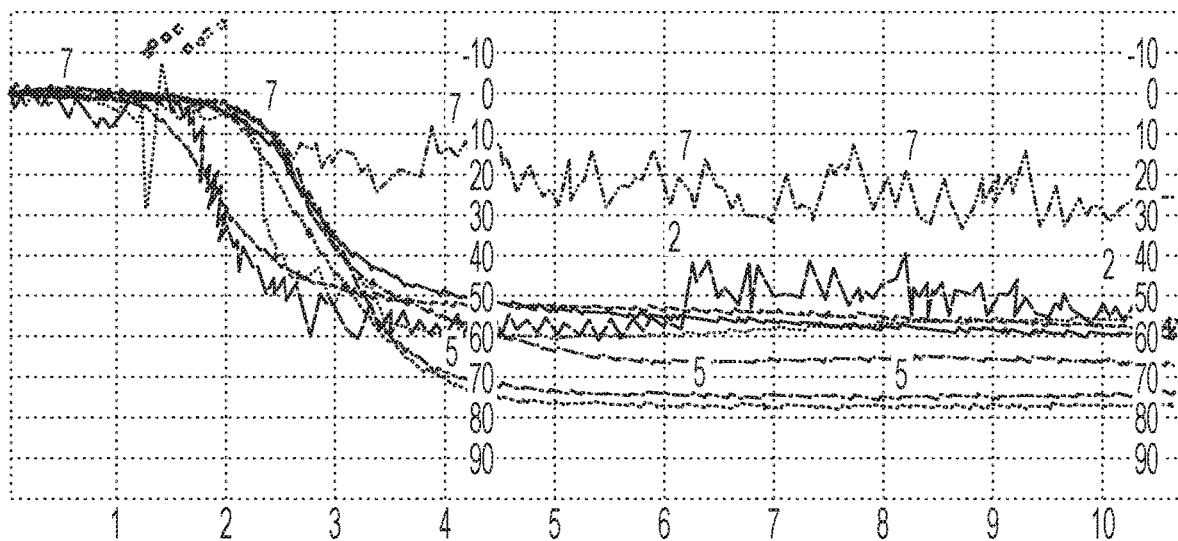
Figure 18:
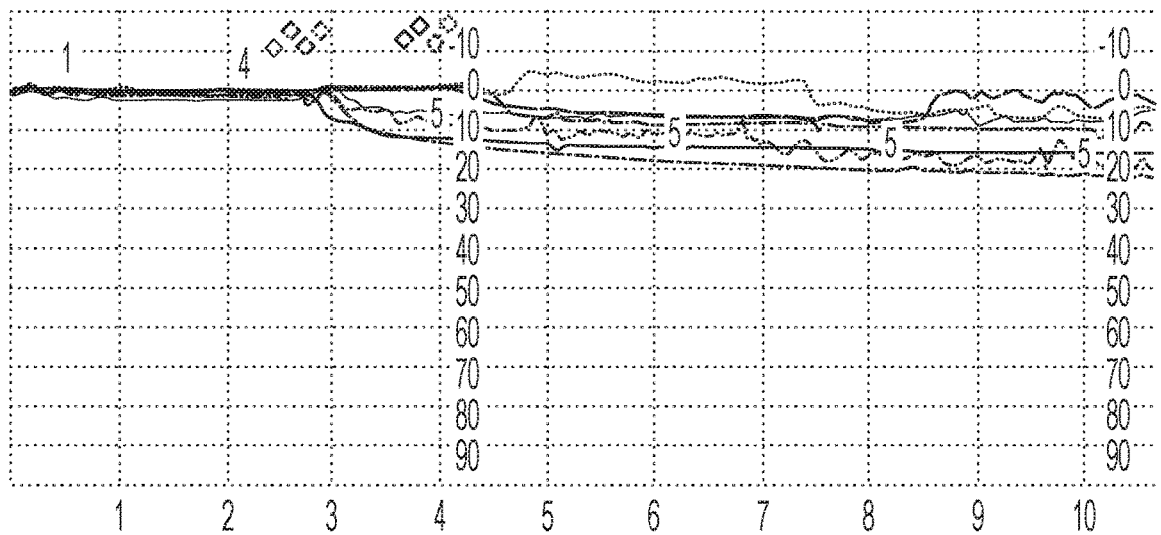
Figure 19:
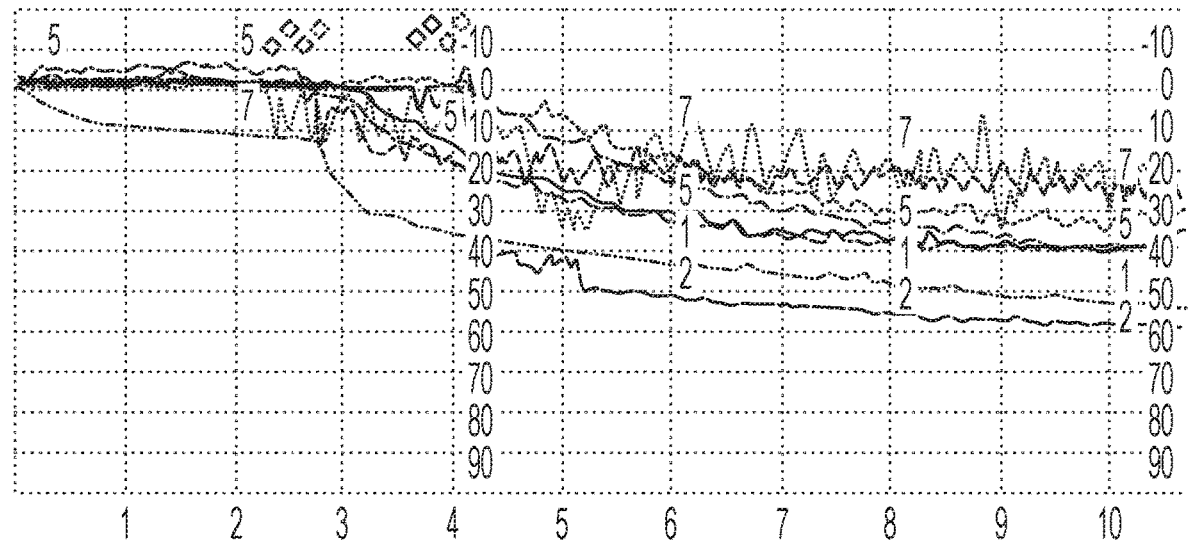
Figure 20:
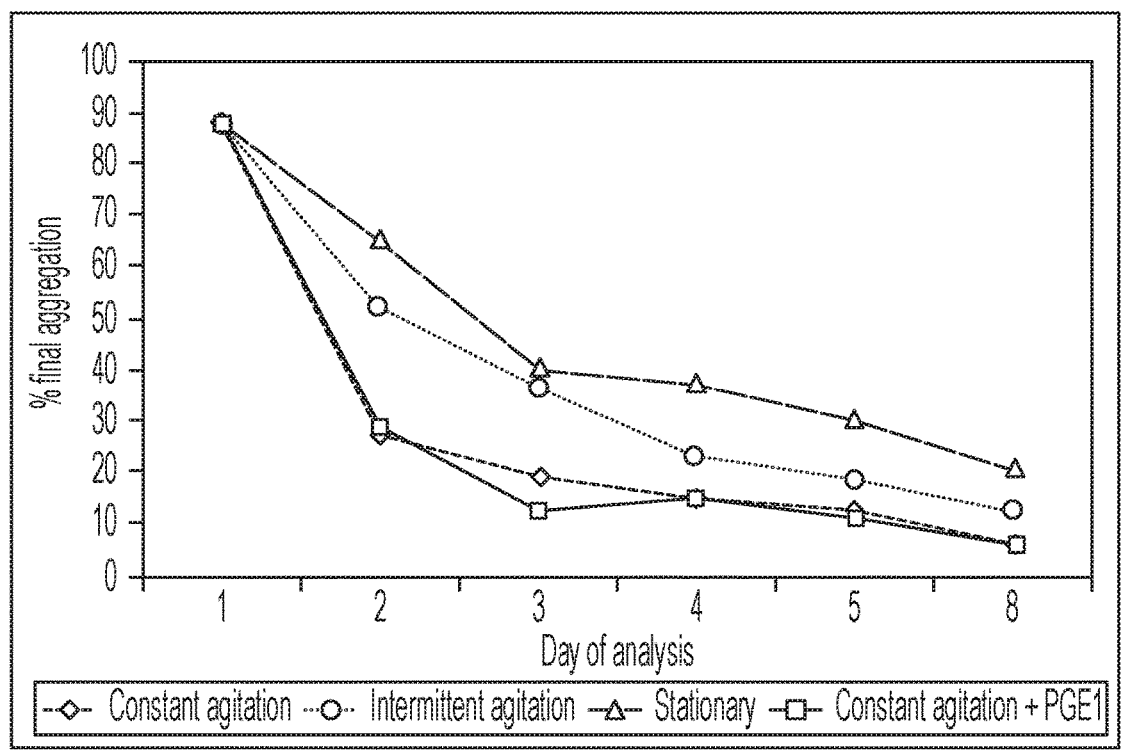
Figure 21:
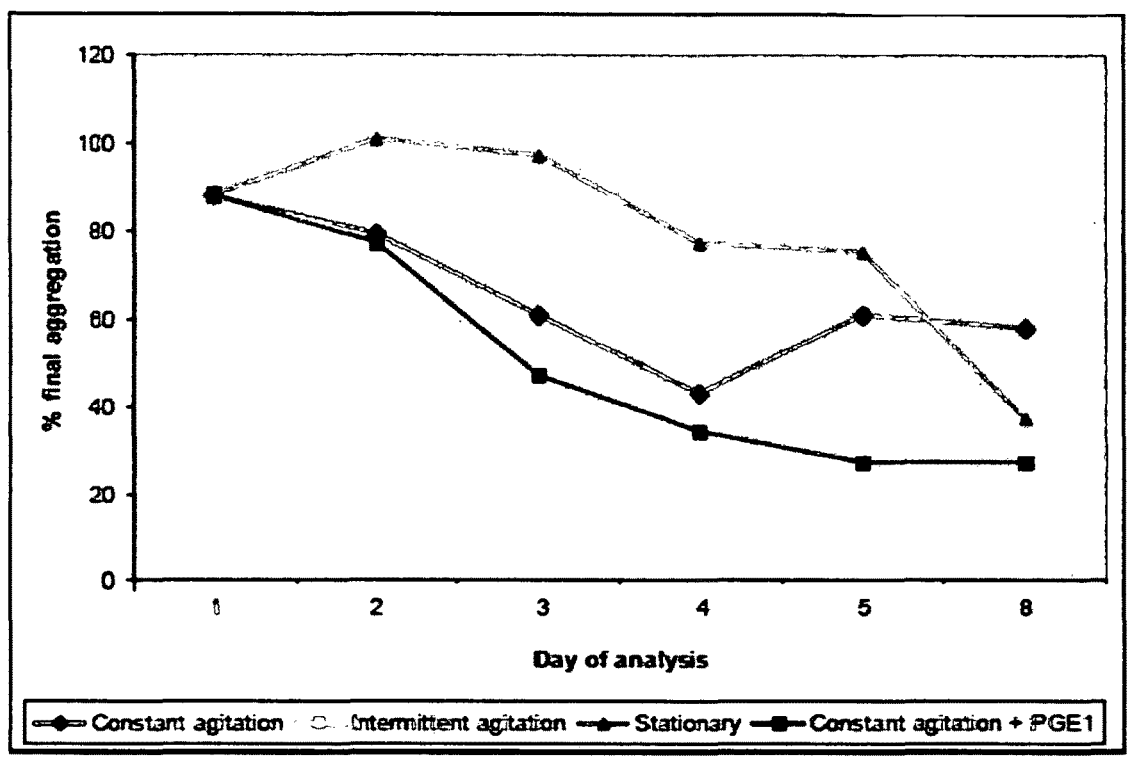

The PDGF-BB present in test samples or standards, the target protein, binds to the capture antibodies and becomes anchored to the plate. A second antibody directed against human PDGF-BB that is conjugated to Biotin is added which binds to the PDGF-BB captured by the first antibody during a two hour incubation. Residual, unbound material is washed off and streptavidin conjugated to the enzyme horse radish peroxidise (HRP) is added to each well. Streptavidin forms strong, non-covalent 1:1 complexes with biotin during a two hour incubation. Residual material is washed off and a substrate for the enzyme, tetramethyl-benzidine, is added. The product of the enzyme-substrate reaction is coloured, the intensity of which is directly proportional to the amount of PDGF-BB in the samples, which is assessed against a standard curve. Diagram reproduced from www.mitosciences.com FIG. 9 shows Collagen-induced aggregation: Day 1. Trace 1 and Trace 3: 10 µg/mL collagen. Trace 2 and Trace 4: 5 µg/mL collagen, FIG. 10 shows Collagen-induced aggregation for PRP stored in Nunc™ flasks: Day 2, Trace 1 and Trace 2 Constant agitation MA: 27% Plt: 257×109/L
Trace 3 and Trace 4 Intermittent agitation MA: 52% Plt: 241×109/L
Trace 5 and Trace 6 Stationary MA: 65% Plt: 228×109/L
Trace 7 and Trace 8 Constant agitation+PGE1 MA: 29% Plt: 243×109/L FIG. 11 shows collagen-induced aggregation for PRP stored in universals: Day 2
Trace 1 and Trace 2 Constant agitation MA: 79% Plt: 149×109/L
Trace 3 and Trace 4 Intermittent agitation MA: 92% Plt: 221×109/L
Trace 5 and Trace 6 Stationary MA: 101% Plt: 215×109/L
Trace 7 and Trace 8 Constant agitation+PGE1 MA: 77% Plt: 149×109/L FIG. 12 shows collagen-induced aggregation for PRP stored in Nunc™ flasks: Day 3, Trace 1 and Trace 2 Constant agitation MA: 19% Plt: 245×109/L
Trace 3 and Trace 4 Intermittent agitation MA: 36% Plt: 202×109/L
Trace 5 and Trace 6 Stationary MA: 40% Plt: 213×109/L
Trace 7 and Trace 8 Constant agitation+PGE1 MA: 12% Plt: 221×109/L FIG. 13 shows collagen-induced aggregation for PRP stored in universals:
Day 3, Trace 1 and Trace 2 Constant agitation MA: 61% Plt: 128×109/L
Trace 3 and Trace 4 Intermittent agitation MA: 88% Plt: 221×109/L
Trace 5 and Trace 6 Stationary MA: 97% Plt: 233×109/L
Trace 7 and Trace 8 Constant agitation+PGE1 MA: 47% Plt: 145×109/L FIG. 14 shows collagen-induced aggregation for PRP stored in Nunc™ flasks: Day 4, Trace 1 and Trace 2 Constant agitation MA: 15% Plt: 223×109/L
Trace 3 and Trace 4 Intermittent agitation MA: 23% Plt: 213×109/L
Trace 5 and Trace 6 Stationary MA: 37% Plt: 209×109/L
Trace 7 and Trace 8 Constant agitation+PGE1 MA: 15% Plt: 213×109/L FIG. 15 shows collagen-induced aggregation for PRP stored in universals:
Day 4, Trace 1 and Trace 2 Constant agitation MA: 43% Plt: 117×109/L
Trace 3 and Trace 4 Intermittent agitation MA: 65% Plt: 236×109/L
Trace 5 and Trace 6 Stationary MA: 77% Plt: 243×109/L
Trace 7 and Trace 8 Constant agitation+PGE1 MA: 34% Plt: 133×109/L FIG. 16 shows collagen-induced aggregation for PRP stored in Nunc™ flasks: Day 5, Trace 1 and Trace 2 Constant agitation MA: 13% Plt: 205×109/L
Trace 3 and Trace 4 Intermittent agitation MA: 18% Plt: 193×109/L
Trace 5 and Trace 6 Stationary MA: 30% Plt: 183×109/L
Trace 7 and Trace 8 Constant agitation+PGE1 MA: 11% Plt: 200×109/L FIG. 17 shows Collagen-induced aggregation for PRP stored in universals:
Day 5, Trace 1 and Trace 2 Constant agitation MA: 61% Plt: 102×109/L
Trace 3 and Trace 4 Intermittent agitation MA: 64% Plt: 222×109/L
Trace 5 and Trace 6 Stationary MA: 75% Plt: 233×109/L
Trace 7 and Trace 8 Constant agitation+PGE1 MA: 27% Plt: 118×109/L FIG. 18 shows Collagen-induced aggregation for PRP stored in Nunc™ flasks: Day 8
Trace 1 and Trace 2 Constant agitation MA: 6% Plt: 191×109/L
Trace 3 and Trace 4 Intermittent agitation MA: 12% Plt: 151×109/L
Trace 5 and Trace 6 Stationary MA: 20% Plt: 146×109/L
Trace 7 and Trace 8 Constant agitation+PGE1 MA: 6% Plt: 186×109/L FIG. 19 shows Collagen-induced aggregation for PRP stored in universals:
Day 8
Trace 1 and Trace 2 Constant agitation MA: 58% Plt: 85×109/L
Trace 3 and Trace 4 Intermittent agitation MA: 39% Plt: 188×109/L
Trace 5 and Trace 6 Stationary MA: 37% Plt: 208×109/L
Trace 7 and Trace 8 Constant agitation+PGE1 MA: 27% Plt: 87×109/L FIGS. 20 and 21 plot the changes in final percentage collagen-induced aggregation over time in PRP variably stored in Nunc™ flasks and universal containers respectively.

Figure 22:
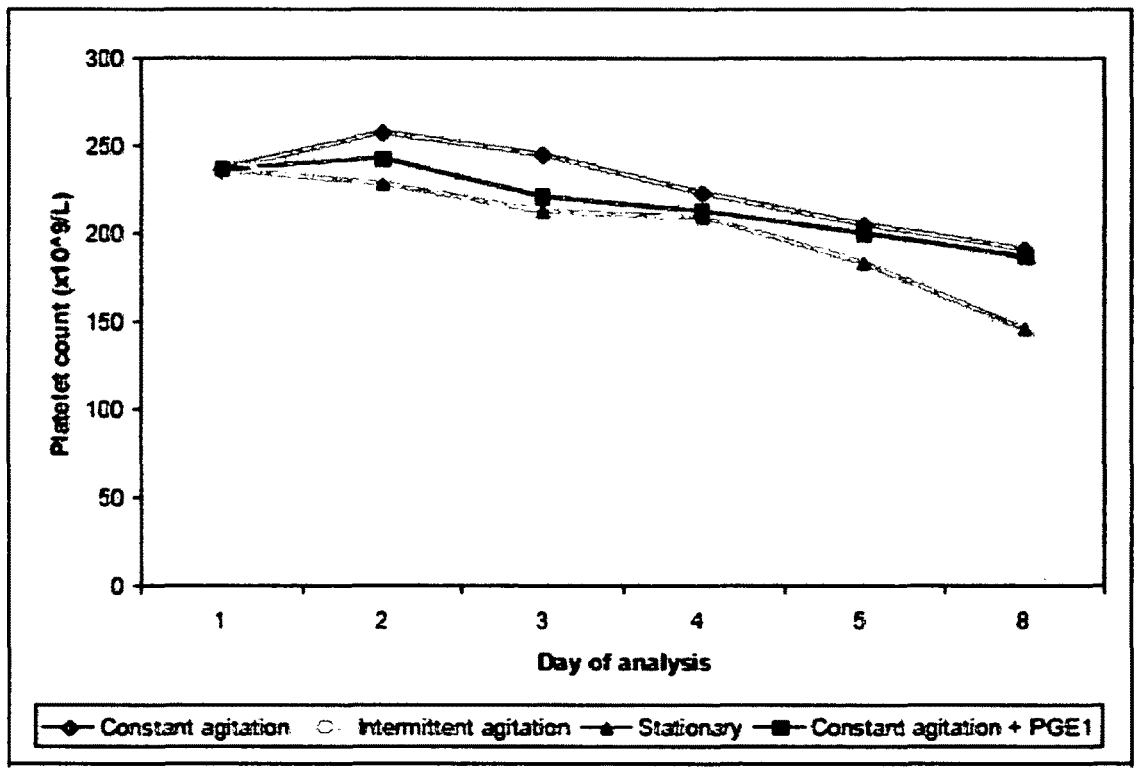
Figure 23:
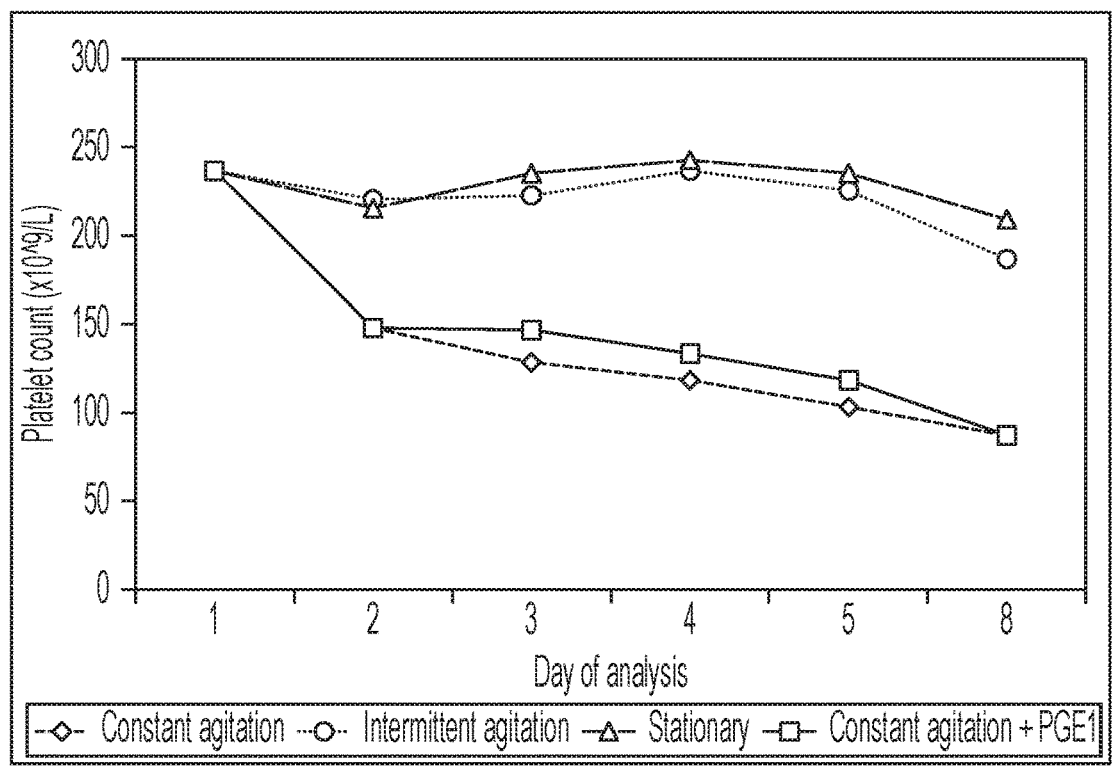

FIGS. 22 and 23 plot the changes in platelet count over time in PRP variably stored in Nunc™ flasks and universal containers respectively.

Figure 24:
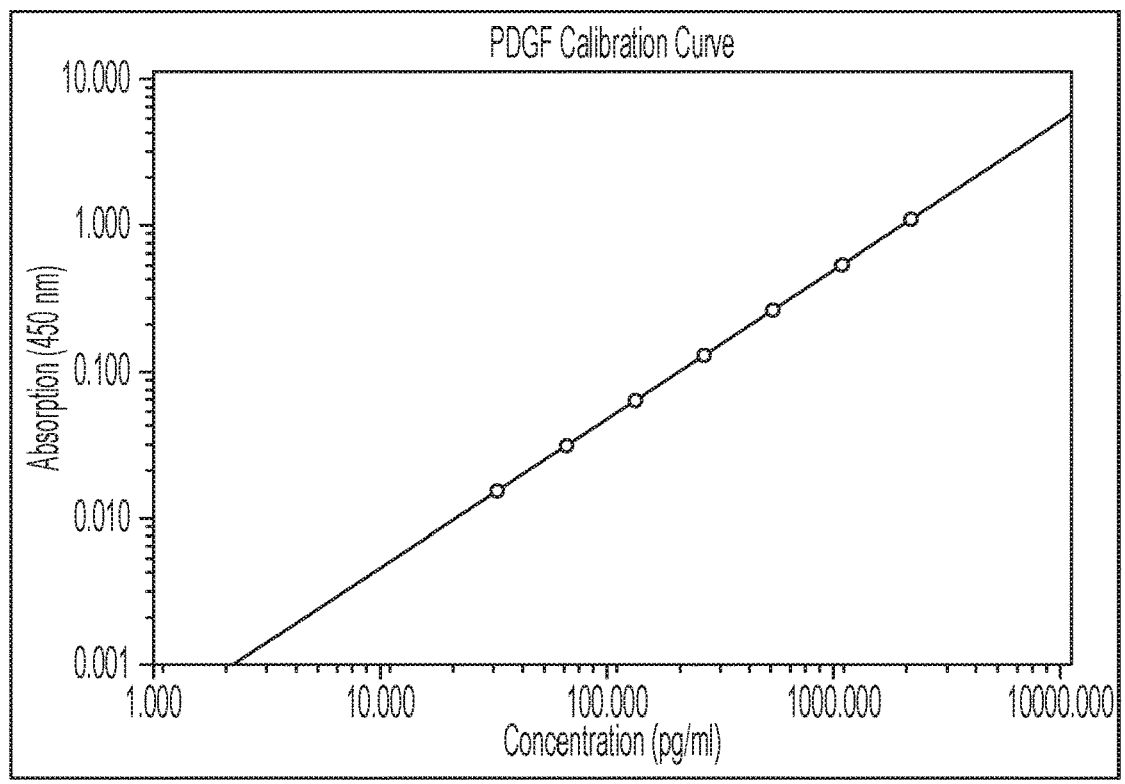
Figure 25:
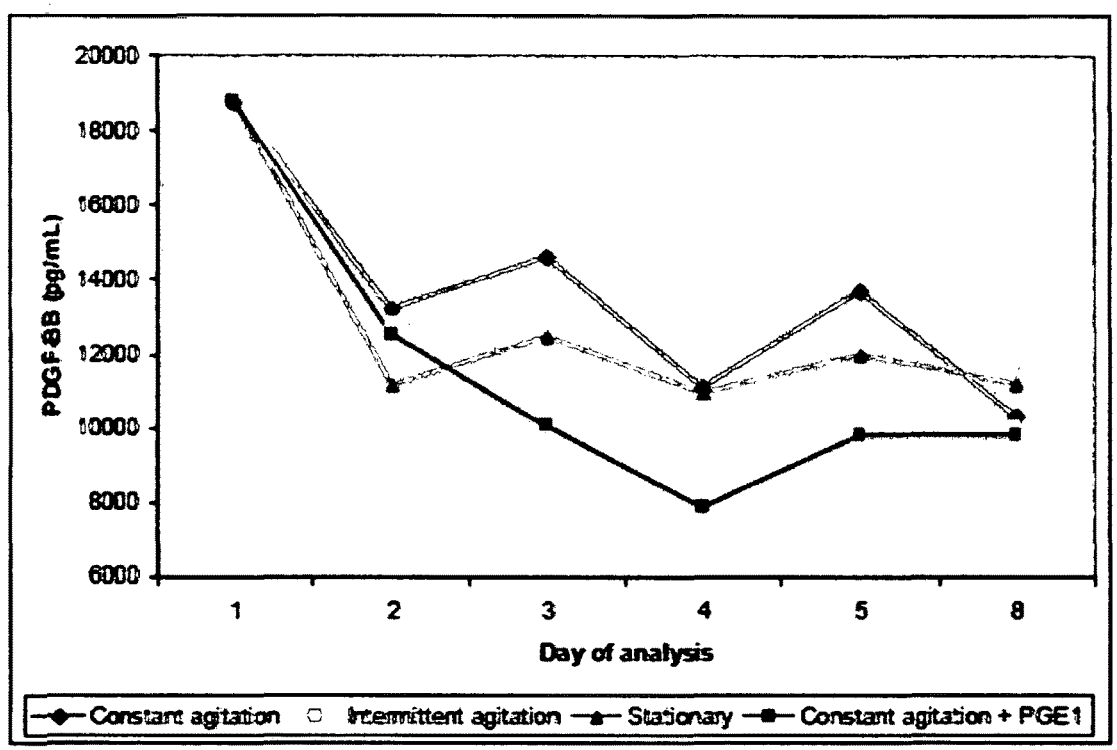
Figure 26:
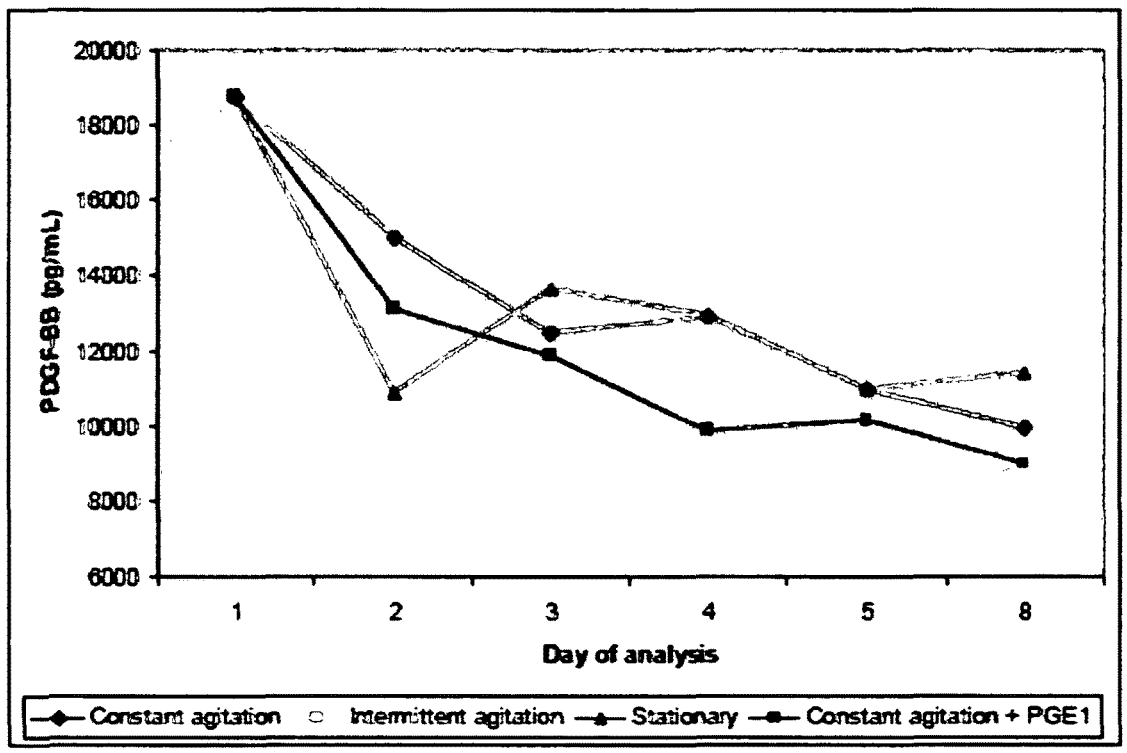

FIG. 24 shows Standard curve for PDGF-BB ELISA,

FIG. 25 shows Plots of supernatant PDGF-BB levels count over time in variably stored PRP FIGS. 25 and 26 plot the PDGF-BB levels in supernatants of collagen-activated PRP that had been variably stored in Nunc™ flasks and universal containers respectively. Serial PDGF-BB levels for supernatants of Nunc™ flask-stored PRP after collagen activation. Note that a nominal level has been entered for the unavailable Day 2 result of constant agitation+PGE1 to permit full graphical plot.

FIG. 26 shows Serial PDGF-BB levels for supernatants of universal-stored PRP after collagen activation. Note that a nominal level has been entered for the unavailable Day 2 result of constant agitation to permit full graphical plot.

Figure 27:
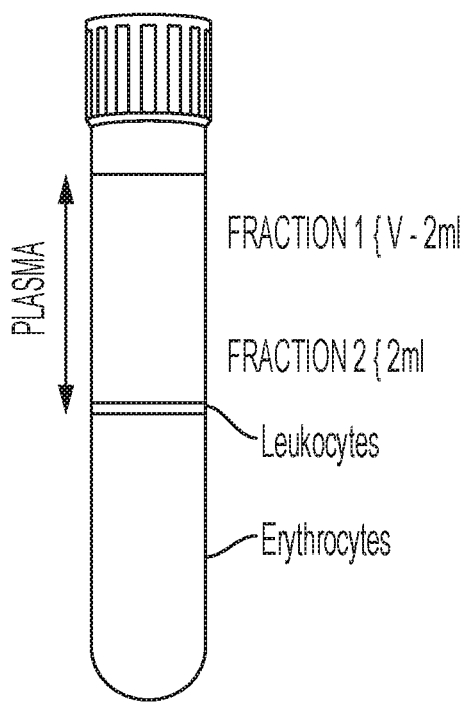

FIG. 27 shows blood that has been separated by centrifugation. Starting from the bottom of each tube the first layer is Erythrocytes, the second very thin layer is of Leukocytes, above the leukocytes is the F2 fraction of the plasma (also called PRP) (about 50% of the plasma) and right on the top is the F1 fraction of the plasma (also called PPP) (the other 50% of the plasma). It is the F2 (PRP) that was used in the tests on platelet storage conditions that are described in this application and it is also the F2 (PRP) fraction that was used in the clinical tests described in this application. F2 fraction is slightly darker than F1 fraction which makes it possible for a practitioner to draw up the F1 fraction first and then F2 fraction separately. The plasma fraction is marked. The plasma fraction is separated into Fraction 1 (F1) (PPP) and Fraction 2 (F2) (PRP). F2 is richer in platelets than F1 and therefore F2 is preferably used in the methods of the present invention.

Figure 28:
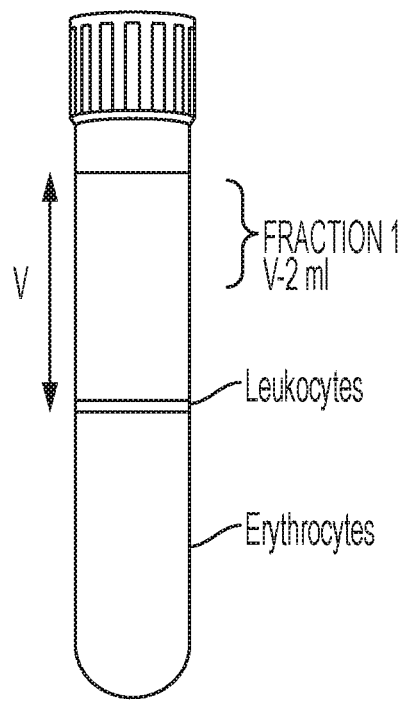

FIG. 28 shows blood that has been separated by centrifugation. Fraction 1 of the plasma (F1) (also called PPP) is marked.

Figure 29:
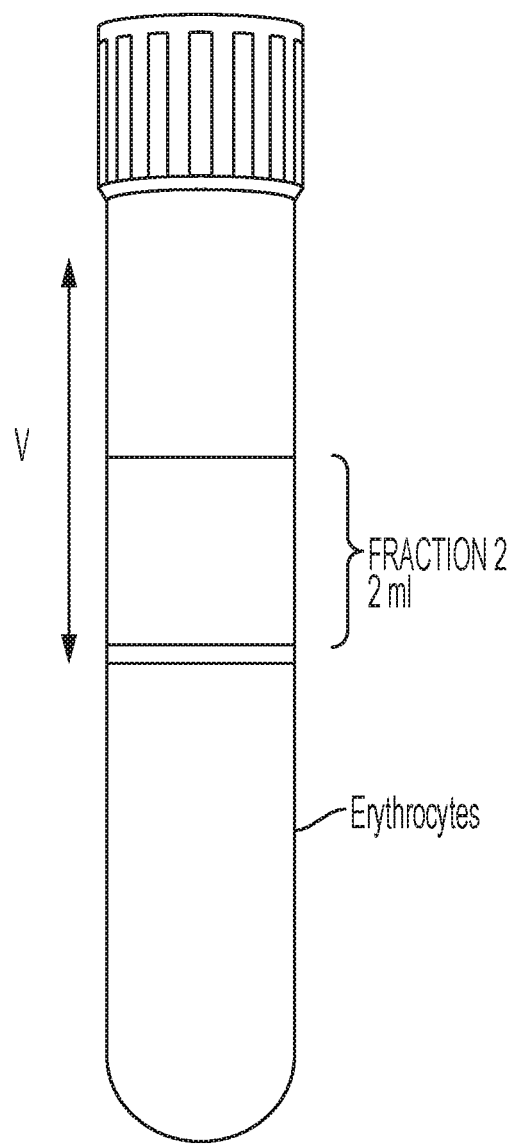
Figure 30:
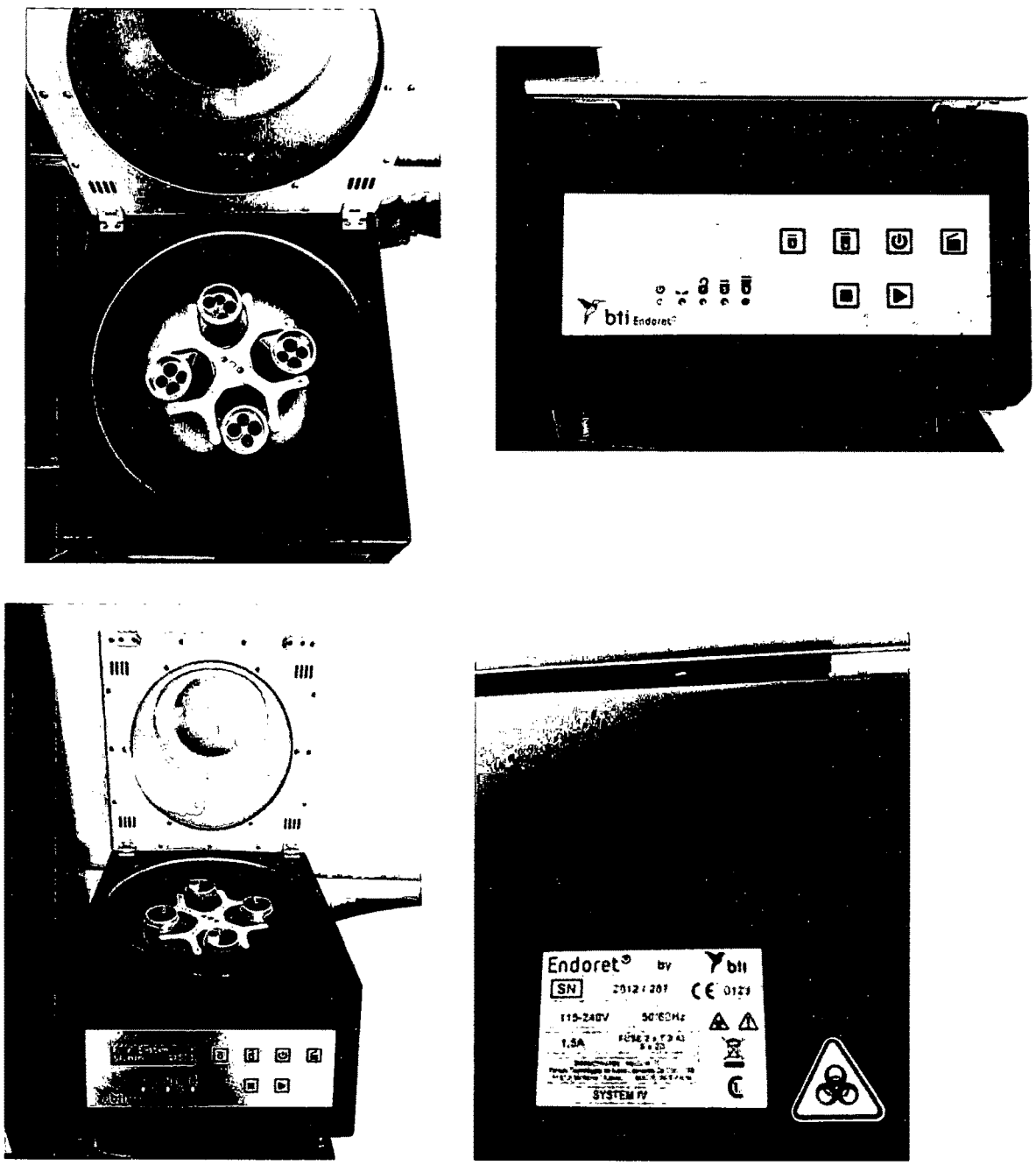

FIG. 29 shows blood that has been separated by centrifugation where the F1 fraction has been removed leaving the F2 fraction, FIG. 30 shows 4 views, from top left clockwise: inside; front; back and front open, of the centrifuge used to separate blood to provide F1 and F2 fractions of plasma. The centrifuge is a BTI-Endornet centrifuge which spins the blood at 580 G for 8 minutes. During the centrifugation process blood gets separated into the fractions described in FIGS. 27 to 29.

Figure 31:
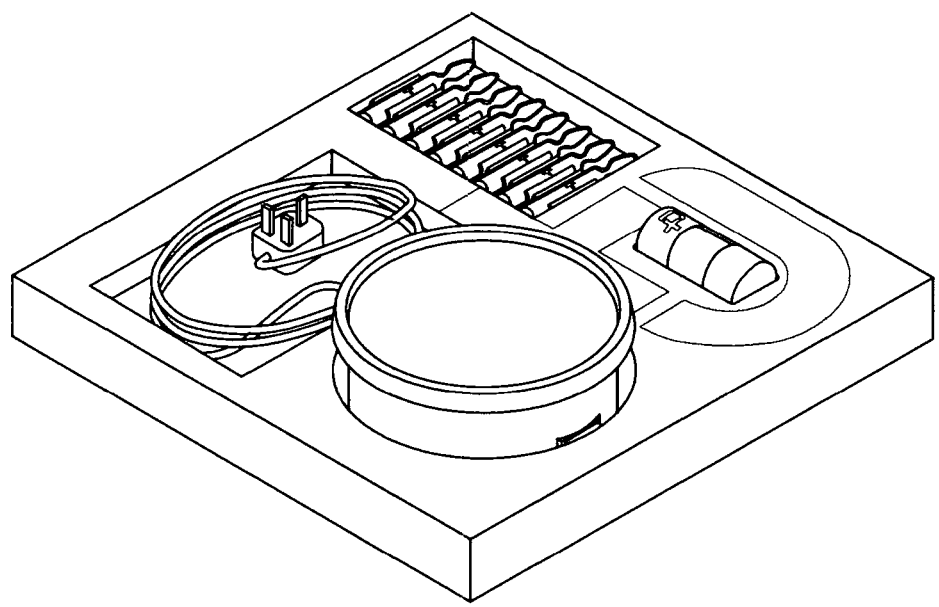

FIG. 31 shows a kit according to the present invention. The kit comprises: a container that is sterile inside for keeping the plasma, PRP or F2 in, this is shown at the right hand side of the figure; several ampules containing the cosmetically acceptable composition, there may be one ampule for each application of the composition to the skin, the ampules are shown at the top of the figure; an agitating device which can be used to constantly agitate the plasma, PRP or F2 inside its container, this is shown at the bottom of the picture.

The cosmetic composition may be: Sun cream, After sun, Foundation, Tinted cream, tinted sun cream, Soothing anti redness cream with the green tint to mask redness of the skin, Scalp serum.

The Growth Factors:

For any PRP, 7 fundamental protein growth factors are concentrated in the plasma after centrifuging (to what degree and with what level of undesirable components will vary)

Platelet-derived growth factors—PDGF-AA, PDGFAB, PDGFBB

Transforming growth factors—TGFB1, TGFB2

Vascular endothelial growth factors—VEGF

Epithelial growth factors—EGF

This concentrate also contains 3 proteins in the blood to act as cell adhesion molecules: fibrin, fibronectin, and vitronectin.

PDFG, VEGF and EGF are the most important for new tissue regeneration.

The carrier may comprising one or more ingredients selected from table 1.

The carrier may comprise

TABLE 1

All items stated include both their Organic and Synthetic versions.

| Item | Function |
|---|---|
| D522 (Dry Flo Plus) | Absorbant |
| D572 (Dry Flo AF) | Absorbant |
| K505 (Kaolin 2747) | Absorbant |
| M742 (Magnesium Carbonate) | Absorbant |
| S813 (Sorbosil BFG50) | Absorbant |
| C936 (Color Clay Rosa) | Absorbant/abrasive |

TABLE 1-continued

All items stated include both their Organic and Synthetic versions.

| Item | Function |
|---|---|
| A577-CC (Alistin P5) | Active against cell membrane damage |
| L592 (Latex LATZ) | Adhesive polymer |
| G513 (Glypure 70) | AHA, pH adjuster |
| L546 (Lactic Acid 90%) | AHA, pH adjuster |
| Z503 (Zincidone) | Anti dandruff |
| A764 (Avenacare Beta Glucan) | Anti oxidant |
| D571-HM (Deepaline PVB) | Anti wrinkle active |
| M704-CC (Matrixyl 3000) | Anti wrinkle active |
| S759 (Syn-tacks) | Anti wrinkle active |
| S761 (Syn-Ake) | Anti wrinkle active |
| C911 (Symglucan) | Anti-ageing active |
| O581-CC (Oxygen Complex LS 9641) | Anti-ageing active |
| C642 (Cabosil M5) | Anticaking agent |
| V506 (Veegum Ultra) | Anticaking agent |
| P564 (Protaderm HA) | Antidandruff active |
| S559 (Sodium Salicylate) | Antimicrobial |
| S965 (Sodium Sulfite) | Antimicrobial |
| B507 (BHT) | Antioxidant |
| O510 (Oxynex K Liquid) | Antioxidant |
| P835 (Phyto Terra Organic Mate) | Antioxidant |
| S578 (Stay C50) | Antioxidant |
| V501 (Vitamin E Acetate (dl-alpha Tocopheryl Acetate)) | Antioxidant |
| V528 (Vitamin A Palmitate (1.7 iu)) | Antioxidant |
| V529 (Vitamin A Palmitate (1.0 ml U/g)) | Antioxidant |
| V550 (Ascorbyl Palmitate) | Antioxidant |
| V551 (Tocopherols Mixed (Natural) INCI: Tocopherol) | Antioxidant |
| V552 (dl-Alpha Tocopherol (INCI: Tocopherol)) | Antioxidant |
| v614 (D-Alpha Tocopherol Natural) | Antioxidant |
| S717 (Sodium Disulfite Extra Pure) | Antioxidant/preservative |
| P822 (Phycosaccharide AIP) | Antioxidant/protective extract |
| M507 (Merquat Plus 3331) | Antistatic agent |
| P739 (Polyquarternium-7) | Antistatic agent |
| HEW574 (Actiphyte of Witch Hazel PG) | Astringent |
| HEW575 (Actiphyte of Horse Chestnut PG) | Astringent/anti inflammatory |
| A589 (Organic *Aloe Vera* Powder 200:1 Freeze Dried) | Botanical extract |
| C582 (Codiavelane) | Botanical extract |
| C755-LM (Crodarom Velvet Flower) | Botanical extract |
| C786-AN (Cosflor Marshmallow HGL-1 (PS)) | Botanical extract |
| C787-AN (Cosflor Mango HGL-1 (PS)) | Botanical extract |
| E560 (*Emblica*) | Botanical extract |
| HEO503 (Green Tea Lipo S) | Botanical extract |
| HEO596 (Organix Marigold PS) | Botanical extract |
| HEW1040 (Witch Hazel Organic) | Botanical extract |
| HEW1066-MB (Green Tea LG) | Botanical extract |
| HEW1085-MB (Ceapro Oat Avenanthramides) | Botanical extract |
| HEW1103-MB (Witch Hazel Distilled, Phenoxyethanol) | Botanical extract |
| HEW1122 (Specifix Chamomile FG) | Botanical extract |
| HEW1130 (Specifix Yarrow 1579) | Botanical extract |
| HEW1136 (Specifix Comfrey Leaf PF) | Botanical extract |
| HEW1154 (Orange Secrets) | Botanical extract |
| HEW503 (Extrait Concombre HG) | Botanical extract |
| HEW505 (*Aloe Vera* 10:1) | Botanical extract |
| HEW596 (NAB Fennel Seed Extract) | Botanical extract |
| HEW643-LL (Witch Hazel) | Botanical extract |
| HEW717 (Extract NAB Red Clover Isoflavones) | Botanical extract |
| HEW822 (Green Tea ECO Extract) | Botanical extract |
| HEW863 (Rosewater) | Botanical extract |
| HEW966 (*Calendula* ECO) | Botanical extract |
| HEW987 (Cosflor Roman Chamomile HGL-1) | Botanical extract |
| P850-CC (Pronalen *Ruscus* Spe) | Botanical extract |
| P909 (Proteasyl LS8951 PW) | Botanical extract |
| R516 (Regu-SEB (331-01)) | Botanical extract |
| R563 (Rosamine R) | Botanical extract |
| R566-CC (Remoduline B El) | Botanical extract |

TABLE 1-continued

All items stated include both their Organic and Synthetic versions.

| Item | Function |
|---|---|
| S981-AN (Slippery Elm Bark Powder) | Botanical extract |
| D642 (Dissolvine GL-38) | Chelating agent |
| N502 (Dissolvine Na2 (EDTA Na2)) | Chelating agent |
| N504 (Dissolvine NA (tetra sodium)) | Chelating agent |
| P666-HM (Procircul 8) | Circulation active |
| A611 (AC Yeast Beta Glucan) | Collagen producing active |
| Z507 (Zinc Oxide EP) | colouring agent |
| C766 (Claritea Prov) | Dark circle/complexion lightening active |
| S586 (Salicylic Acid) | Denaturant |
| P831 (Proteasyl TP POE LS 9818) | Elasticity active |
| B515 (Butylene Glycol) | Emolient |
| B586 (Cocoa Butter (Blanova)) | Emolient |
| C534 (Cetiol OE) | Emolient |
| C581 (Cetiol V) | Emolient |
| C608 (Organic Cupuacu Butter Refined Grade) | Emolient |
| C673 (Cocoa Butter) | Emolient |
| C760 (Cetiol C5) | Emolient |
| C918 (Cetiol AB) | Emolient |
| D585 (Dragoxat 89) | Emolient |
| D783 (DC245) | Emolient |
| G523 (Glucamate LT) | Emolient |
| G549 (Glucamate SSE20) | Emolient |
| G550 (Glucate SS) | Emolient |
| H568 (Heliogel) | Emolient |
| H592-HM (Hexyl Laurate) | Emolient |
| H593 (Hydrogenated Polyisobutene) | Emolient |
| HEO502 (*Aloe Vera* Oil Extract CG) | Emolient |
| I512 (Isopropyl Palmitate) | Emolient |
| I513 (Isopropyl Myristate) | Emolient |
| I564 (Isopropyl Myristate) | Emolient |
| I569 (Isononyl Isononanoate (Dubb ININ)) | Emolient |
| I570 (Isopropyl Isostearate) | Emolient |
| L548 (Lipovol MOS-70) | Emolient |
| L595 (Linosa PEG-7 Glyceryl Cocoate) | Emolient |
| L642 (Lipex Shea) | Emolient |
| L645 (Lipex Sheasoft) | Emolient |
| M726 (Mikrokil Cos (12002)) | Emolient |
| OIL503 (Almond Oil (Sweet) - Refined) | Emolient |
| OIL506 (Jojoba Oil Light) | Emolient |
| OIL511 (Grapeseed Oil) | Emolient |
| OIL512 (Avocado Oil) | Emolient |
| OIL520 (Peach Kernel Oil) | Emolient |
| OIL522 (Soybean Oil) | Emolient |
| OIL533 (Blackcurrant Seed Oil) | Emolient |
| OIL536 (Olive Oil - Refined) | Emolient |
| OIL541-AN (Castor Oil, Refined) | Emolient |
| OIL568 (Organic Jojoba Oil) | Emolient |
| OIL572 (Organic Coconut Oil) | Emolient |
| OIL574-AN (Hemp Oil, Refined) | Emolient |
| OIL590 (Organic Grapeseed Oil) | Emolient |
| OIL593 (*Calendula* Oil 1210) | Emolient |
| OIL599 (Organic Shea Butter) | Emolient |
| OIL606 (Organic Sweet Almond Oil) | Emolient |
| OIL613 (Organic Evening Primrose Oil) | Emolient |
| OIL614 (Organic Wheatgerm Oil) | Emolient |
| OIL619 (*Camelina* Oil Refined) | Emolient |
| OIL621 (Organic Almond Oil) | Emolient |
| OIL633 (Coconut Oil - Fractionated (liquid)) | Emolient |
| OIL638 (Rapeseed Oil Refined) | Emolient |
| OIL655 (Coconut Oil RD) | Emolient |
| OIL658 (Herbal Extract *Aloe Vera* Oily) | Emolient |
| OIL659 (Sunflower Oil Refined) | Emolient |
| OIL661 (Jojoba Oil, Golden) | Emolient |
| OIL669 (Mineral Oil BO) | Emolient |
| OIL676 (Tea Tree Oil Organic) | Emolient |
| OIL678 (Olive Oil, Organic) | Emolient |
| OIL686 (Avocado Oil Refined) | Emolient |
| OIL706 (Organic Castor Oil) | Emolient |
| OIL722 (*Macadamia* Oil Organic) | Emolient |
| OIL729-NK (Tamanu Oil, stabilised) | Emolient |
| OIL734-CC (Corn Oil Refined) | Emolient |
| OIL751 (Hazlenut Oil, Refined) | Emolient |
| OIL756 (Rosehip Oil, Refined) | Emolient |
| OIL809 (Organic Safflower Oil) | Emolient |
| OIL830 (Soyabean Oil Refined) | Emolient |
| OIL831 (Lady's Thistle Oil) | Emolient |
| OIL841 (Meadowfoam Seet Oil) | Emolient |
| OIL853 (Avocado Oil, Crude) | Emolient |
| OIL867-AN (Babobab Oil Organic) | Emolient |
| OIL870 (*Calendula* Oil) | Emolient |
| OIL907 (Organic Deodorised Argan Oil) | Emolient |
| S1014 (Silicone CM56 (DC345)) | Emolient |
| S1050 (Saboderm ISN) | Emolient |
| S510 (Stearyl Alcohol) | Emolient |
| S523 (Silicone DC 200 Fluid 350 CST (see B665)) | Emolient |
| S574 (Silicone DC 200/100) | Emolient |
| S575 (Silicone DC 1501) | Emolient |
| S614 (Silicone DC 245) | Emolient |
| V588-AN (Viatenza Shea PO6) | Emolient |
| W516 (Wickenol 156 (replaces L503)) | Emolient |
| T527 (Tegosoft LSE 65K Soft) | Emolient/foam enhancer/viscosity modifier |
| A504 (Amphisol K) | Emulsifier |
| A633-AN (Axol C 62 Pellets) | Emulsifier |
| C736 (Span 60-PA-(SG) (previoulsy Crill 3 - sorbitan stearate)) | Emulsifier |
| C750-CC (Crovol A70 UK) | Emulsifier |
| C813 (Crodafos CES) | Emulsifier |
| C815 (Ceteareth 25) | Emulsifier |
| C933-CC (Cetyl Palmitate 95%) | Emulsifier |
| D609 (Dermofeel SL) | Emulsifier |
| E529 (Euperlan PK 1200) | Emulsifier |
| E633 (Edenor C12 98-100 MY) | Emulsifier |
| K570 (Kemest GDS) | Emulsifier |
| K571 (Kemionic SLES 228) | Emulsifier |
| L536 (Lexemul 561) | Emulsifier |
| L583 (Lexemul T) same as G621) | Emulsifier |
| L601 (Linosa SLES 70) | Emulsifier |
| M519 (Montanov 68) | Emulsifier |
| M550 (Montanov 202) | Emulsifier |
| M564 (Montanov S) | Emulsifier |
| P559 (Procol CS-20D) | Emulsifier |
| P680 (Procol CS 20 (Ceteareth-20)) | Emulsifier |
| P869-MB (Palmitic Acid) | Emulsifier |
| S748 (Surfac JH 200) | Emulsifier |
| S840 (Surfhope SE Cosme C-1616) | Emulsifier |
| T609 (Tegosoft PC41) | Emulsifier |
| S677 (Surfac UN90) | Emulsifier/degreasing agent |
| H554-SD (Hydramol TGL Ester) | Emulsifier/skin conditioning agent |
| S976 (Sveltine LDRM 961S) | Emulsifier/skin conditioning agent |
| S718 (Sorbitan Mono Stearate) | Emulsifier/surfactant |
| C810 (Surface CS (Cetearyl Alcohol)) | Emulsioin stabiliser |
| B648 (Organic Beeswax) | Emulsion stabiliser |
| B661 (Beeswax, white granules (8104)) | Emulsion stabiliser |
| C674 (Cetyl Alcohol) | Emulsion stabiliser |
| E566 (Emulium Kappa) | Emulsion stabiliser |
| M606 (Montanov L) | Emulsion stabiliser |
| S1003 (Stearic Acid) | Emulsion stabiliser |
| S505 (Stearic Acid 1810) | Emulsion stabiliser |
| HEW602 (NAB Willow Bark Extract) | Exfoliating BHA |
| E530 (Peeling Enzymatique) | Exfoliator |
| F561 (Florabeads 28/60 Arizona Sky) | Exfoliator |
| P521 (Pumice Powder Coarse (50 mesh)) | Exfoliator |
| T614 (Tabishirex) | Exfoliator |
| A607 (Antileukine 6) | Extract with UV protection |
| HEW672 (NAB *Arnica* Extract) | Eye active (inflammation/puffiness) |
| L606 (Liponate ISA) | Fatty acid |
| L565 (Luviset Clear) | Film former |
| L727 (Luviskol K30) | Film former |
| P657 (Pepha-Tight) | Film former |
| D683 (Daitosol 5500GM K-5136) | Film former |
| C759 (Covacryl SP) | Film former/conditioning agent |

TABLE 1-continued

All items stated include both their Organic and Synthetic versions.

| Item | Function |
|---|---|
| C762-SD (Copolymer 845 G) | Film former/conditioning agent |
| E531 (Egg White Powder P11) | Film former/conditioning agent |
| L713 (Luviquat UltraCare) | Film former/hair fixative |
| M663 (Mirustyle XHP) | Film former/hair fixative |
| B643 (Biopeptide EL) | Firming active |
| T682-CC (Tensine) | Firming active |
| T685-CC (Tensine 2) | Firming active |
| HEW671 (Extract NAB Mushroom) | Firmness and anti wrinkle active |
| S696 (Sodium Bicarbonate) | Fizzing agent |
| A640 (GLB60 (Antil HS 60) | Foam booster/viscosity modifier |
| D625 (DC949 Cationic Emulsion) | Hair conditioning agent |
| M644 (Mirustyle MFP PE) | Hair conditioning agent |
| S979-SD (Stylese CC10) | Hair conditioning agent |
| T666 (Tinocare SiAl) | Hair conditioning agent |
| V603-AN (Varisoft 432 CG) | Hair conditioning agent |
| V606-AN (Varisoft BTMS Flake) | Hair conditioning agent |
| K558 (Keratec IFP PE) | Hair/skin conditioning agent |
| G537 (Glycerin (Surfac G995V)) | Humectant |
| G540 (Organic Glycerine) | Humectant |
| G628 (Organic Glycerin) | Humectant |
| HEW585 (Extrait Ginseng HG) | Humectant |
| HEW677 (Extract NAB Siberian Ginseng) | Humectant |
| L549 (Lubragel Oil) | Humectant |
| L556 (Lactofill Sensitive) | Humectant |
| L622-CC (Lubrajel PF) | Humectant |
| L717 (Lubrajel Oil Free) | Humectant |
| P501 (Propylene Glycol) | Humectant |
| P553 (D-Panthenol 751 (liquid)) | Humectant |
| P668 (Protachem GL26 (same as L616)) | Humectant |
| S521 (Squalane - Olive Derived (was D527)) | Humectant |
| S522 (Sodium Hyaluronate 1% Solution (Liquid)) | Humectant |
| S545 (Sorbitol Syrup 70% (Sorbidex NC 16205)) | Humectant |
| S771 (Sodium Hyaluronate Salt (Powder)) | Humectant |
| W503 (Waglinol 6014 (IPM)) | Imolient |
| S676 (Solaveil CT-100 Clarus) | Inorganic sunscreen |
| Z502 (Zinc Oxide CM3K 50 XZA) | Inorganic sunscreen |
| S789 (Suberlift) | Lift active |
| N600-CC (Nano LPDs Arbutin PF) | Lightening active |
| S952 (Surfac HT10) | Low foam surfactant |
| B610 (Bamboo Exfoliator 500) | Micro exfoliator |
| D545 (Diamond Powder SY-FS 60/70) | Micro exfoliator |
| P601 (Pearl Powder 125) | Micro exfoliator |
| R557 (Rice Exfoliator 500) | Micro exfoliator |
| I561 (Isocell MAP) | Microencapsulated antioxidant |
| U532-CC (UV Titan M 262) | Mineral/inorganic sunscreen |
| N598-CC (Norgel) | Moisturiser |
| H594-CC (Hydrosoy 2000 PE) | Moisturising |
| L547 (Lamesoft PO65) | Moisturising |
| V534-CC (Viamerine 4000) | Moisturising |
| T557 (Tagravit F1) | Moisturising/anti-ageing |
| K562 (Kahl Berry Wax 6290) | Natural wax, texturiser |
| A562 (Acusol OP 301) | Opacifier |
| M727 (Myristic Acid PC) | Opacifier |
| T687 (Tego Pearl N300) | Pearliser |
| C510 (Citric Acid Monohydrate) | pH adjuster |
| P886 (Potassium Hydroxide) | pH adjuster |
| S517 (Sodium Hydroxide) | pH adjuster |
| S960 (Sodium Hydroxide 45% solution) | pH adjuster |
| T501 (Triethanolamine 99% (T.E.A)) | pH adjuster |
| C536 (Calcium Carbonate) | pH buffer |
| T691 (Tris Amino Ultra PC) | pH buffer |
| G569 (Gelinnov) | Polymer |
| L715 (Luvigel EM) | Polymer/skin conditioning agent |
| D589 (Dermosoft Octiol) | Preservative |
| G609 (Geogard 221) | Preservative |
| P590 (Potassium Sorbate Granules 105119) | Preservative |
| PR502 (Nipagin M) | Preservative |
| PR504 (Kathon CG) | Preservative |
| PR505 (Nipasol M) | Preservative |
| PR506 (Nipastat) | Preservative |
| PR508 (Phenonip) | Preservative |
| PR510 (Phenoxetol (Phenoxyethanol) use PR572) | Preservative |
| PR515 (Germaben II) | Preservative |
| PR518 (Euxyl K100) | Preservative |
| PR526 (Euxyl K702) | Preservative |
| PR533-CC (Paratexin CPS (Chlorphenesin)) | Preservative |
| PR546 (Germall 115 USP (Powder)) | Preservative |
| PR547 (Euxyl PE 9010) | Preservative |
| PR548 (Grapefruit Seed Extract G2) | Preservative |
| PR561 (Optiphen) | Preservative |
| PR563 (Benzyl Alcohol) | Preservative |
| PR568 (Sodium Benzoate) | Preservative |
| PR572 (Saliethanol (phenoxyethanol)) | Preservative |
| PR580 (Geogard Ultra) | Preservative |
| PR585 (Sorbic Acid) | Preservative |
| PR588-LM (Euxyl K712) | Preservative |
| PR593 (Euxyl K701) | Preservative |
| PR595 (Elestab CPN) | Preservative |
| PR607 (BlagGuard GPL (same as PR537)) | Preservative |
| S963-CC (Symdiol 68T (177441)) | Preservative booster/antioxidant |
| S950 (Sensiva SC 10) | Preservative/emolient |
| HEW675 (Actiphyte of White Tea GL) | Protective |
| I546 (Protanal FM 6130 (Isagel FM Alginate)) | Setting agent |
| A774 (Avenacare ECO Oat Beta Glucan) | Skin and hair rejuvenation |
| HEW963 (Oligophycocorail SPE) | Skin balancing |
| A734 (Aloe Vera Gel Base) | Skin calming |
| HEW885 (Horsetail Extract (1552)) | Skin conditioning |
| HEW896 (Camomile ECO) | Skin Conditioning |
| A502 (Allantoin 98.9%) | Skin Conditioning Agent |
| A676-AN (Aquarich) | Skin conditioning agent |
| A732-CC (AC Oak Kernel Protein Powder) | Skin conditioning agent |
| B503 (Bernel Ester TCC) | Skin conditioning agent |
| C577 (Cosmocair C100) | Skin conditioning agent |
| C698 (Cytobiol Lumin Eye) | Skin conditioning agent |
| C949-CC (Cetiol S) | Skin conditioning agent |
| C954-CC (Cegesoft C24 (same as T526)) | Skin conditioning agent |
| D564 (DC556) | Skin conditioning agent |
| D654-AN (Dermofeel P-30) | Skin conditioning agent |
| F509 (Fucogel 1000PP) | Skin conditioning agent |
| F541 (Fucogel 1.5P) | Skin conditioning agent |
| G563 (Gatuline Age Defence 2) | Skin Conditioning agent |
| G589-AN (Gluadin Wlm Benz) | Skin conditioning agent |
| G605 (Gatuline Skin Repair Bio) | Skin conditioning agent |
| G631 (Gatuline RP) | Skin conditioning agent |
| I560 (Isododecane (CSI Code 5108)) | Skin conditioning agent |
| K567-AN (Kapilarine) | Skin conditioning agent |
| M543 (Mango Butter Refined) | Skin conditioning agent |
| M625 (Myritol 312) | Skin Conditioning agent |
| P556 (Peg 8) | Skin conditioning agent |
| P658 (Pentavitin) | Skin Conditioning agent |
| S804 (Shea Butter, Refined) | Skin conditioning agent |
| S825-CC (DC2501 Cosmetic Wax) | Skin conditioning agent |
| S982-AN (Sunflohair) | Skin Conditioning agent |
| U502 (Urea) | Skin conditioning agent |
| V509 (Vitamin F Glycerinester O/S) | Skin conditioning agent |
| V546 (Vitamin A (Water Miscible) Type 100) | Skin conditioning agent |
| A629-CC (AC Zaatt) | Skin conditioning and lightening agent |
| A653 (Achromaxyl IS) | Skin lightening agent |
| B677 (Belides ORG) | Skin lightening agent |
| P779 (Phytexcell Mulberry) | Skin lightening extract |
| D647 (Dismutin J PF) | Skin protecting antioxidant |
| S1010 (Schercemol 1688 Ester) | Skin/hair conditioning agent |
| T709 (Triethylhexanoin) | Skin/hair conditioning agent |
| P839 (Peptan SR Marine) | Skin/hair conditioning gent |
| D523-LL (Solubiliser 660352) | Solubiliser |
| N608 (Natragem S140NP) | Solubiliser |

TABLE 1-continued

All items stated include both their Organic and Synthetic versions.

| Item | Function |
|---|---|
| P519 (Polysorbate 60 (Protasorb S-20 NF)) | Solubiliser |
| P587 (Protasorb O-20) | Solubiliser |
| P622-HM (Procol OA-20) | Solubiliser |
| P646 (Protachem HCO 40) | Solubiliser |
| P880 (PEG-20 Glyceryl Laurate (Tagat L2)) | Solubiliser |
| S535 (Surfacare T20) | Solubiliser |
| S564 (Solubilisant LRI) | Solubiliser |
| C951 (Crillet 3 (Tween 60-SS)) | Solubiliser/emulsifier |
| C719-CC (Cibafast H Liquid) | Solvent |
| E504 (Ethanol DEB 100) | Solvent |
| T619 (Transcutol CG) | Solvent |
| HEW980-CC (Cosflor Cucumber HGL-1 (PS)) | Soothing |
| P823-HM (Phytexcell Centaury) | Soothing/astringent extract |
| A604 (Aquacacteen) | Soothing/calming/firming extract |
| HEW673 (Authenticals of Cucumber) | Soothing/calming/firming extract |
| S823 (Syntran PC5227CG) | SPF booster |
| HEW625 (Actiphyte of Paraguay Tea Conc.) | SPF booster/irritancy reducer of AHA's |
| M735 (MALTODEXTRIN (replaces D529)) | Stabiliser |
| O564-LL (Oxynex ST Liquid) | Sunscreen stabiliser |
| A542 (Steol CA-330-E (AES 136)) | Surfactant |
| C777-CC (Crodasinic LS 30) | Surfactant |
| D566 (Dehyton K (Sabosol PB)) | Surfactant |
| H523 (Hostapon SCI 85 G (Granular)) | Surfactant |
| H540 (Hostapon CT TEIG) | Surfactant |
| K569 (Kemthox FA S 21 (P776)) | Surfactant |
| O523 (Oramix CG 110 (Sue Stowell)) | Surfactant |
| O532 (Oramix NS 10) | Surfactant |
| P527 (Plantacare 2000 UP (Kemgluco CEHL)) | Surfactant |
| P534-AN (Plantacare 818) | Surfactant |
| P538 (Kemgluc CLM Plantacare 1200 UP) | Surfactant |
| P879 (Procetyl AWS) | Surfactant |
| S1047 (Steol CS-330) | Surfactant |
| S547-LM (Surfac GMS NSE40) | Surfactant |
| S710 (Stepanol AM 30) | Surfactant |
| T512 (Tegobetaine F50) | Surfactant |
| V599 (Varisoft 300) | Surfactant |
| S766 (Steol BES70 D5) | Surfactant/emulsifier |
| S777 (Sucragel CF) | Surfactant/emulsifier |
| V511 (Varisoft BT85 (Pellets)) | Surfactant/hair conditioning agent |
| S795 (Surfacare DHA) | Tanning agent |
| E576-HM (Erythrulose) | Tanning enhancer |
| C920 (Covabead PMMA) | Texturising effect |
| B673 (BRG SG 116 (DC 9040)) | Texturising Silicone |
| C503 (Carbopol Ultrez 10) | Thickener |
| X507 (Xperse 201) | UV broad spectrum protection |
| S699 (Sunspheres Powder) | UV protection |
| T683 (Tinosorb M) | UVA absorber |
| UV504 (Uvinul MS40 (Benzophenone-4)) | UVA absorber |
| UV505 (Parsol 1789) | UVA absorber |
| UV514 (Uvinul A Plus Granular) | UVA absorber |
| Z505 (Z-Cote HP1) | UVA and UVB protection |
| UV510 (Eusolex 4360 (Benzophenone-3)) | UVA/B absorber |
| E571 (Eusolex t-2000) | UVB absorber |
| UV502 (Parsol MCX) | UVB absorber |
| UV525-CC (Escalol 587) | UVB absorber |
| C955 (Carbopol 980) | Viscosity control |
| L721 (Lexfilm Sun) | Viscosity control |
| M565 (Mackol CAS 100N) | Viscosity control |
| V527-CC (Viscarin GP209NF) | Viscosity control |
| A539 (Aculyn 28) | Viscosity modifier |
| A601 (Amigel) | Viscosity modifier |
| C584 (Carbopol Ultrez 21) | Viscosity modifier |
| C594 (Carbopol Ultrez 20) | Viscosity modifier |
| H555-HM (Wacker HDK H20) | Viscosity Modifier |
| K502 (Keltrol F) | Viscosity Modifier |
| K531 (Keltrol CG TE) | Viscosity Modifier |
| K532 (Keltrol CG-RD) | Viscosity Modifier |
| K537 (Keltrol CG SFT) | Viscosity Modifier |
| L651 (Lanette D) | Viscosity modifier |
| M528 (Methocel J75 MS) | Viscosity Modifier |
| N509 (Natrosol 250 HHR) | Viscosity Modifier |
| N533 (Natrosol Plus CS Grade 330) | Viscosity Modifier |
| P530 (Pemulen TR 2) | Viscosity Modifier |
| S589 (Structure XL) | Viscosity modifier |
| S723 (Simulgel NS) | Viscosity modifier |
| A554-HM (Antil 171) | Viscosity modifier for surfactants |
| S544 (Sepigel 305 x 4) | Viscosity modifier/emulsifier |
| A766 (Avicel PC-611) | Viscosity modifiers |
| S1036 (Sylvaclear A200V) | Waterproofing |
| S501 (Sodium Chloride (salt)) | |
| C905 (Organic Cocoa Butter) | |
| Collagen Ingredients | |
| Marine Hydrolysed Collagen LMW | Hydrolysed Collagen (Marine) |
| Collagen 1% | Soluble collagen (porcine) |
| Collagen Hydrolysate Cosmetic N-SS | Hydrolysed Collagen |
| Solu-Coll Native | Soluble Collagen (Cattle) |
| Solu-Coll M | Soluble Collagen (Marine) |
| Solu-Mar Native | Soluble Collagen (Marine) |
| Dermosot 1388 | Preservative |
| Retinol (tretinoin) | Preservative |
| Saponin | Preservative |
| Q Enzyme 10 | Preservative |
| Glycerrhinitic Acid | Preservative |
| Fragrances | |
| FRAG1065 (Fresh Style PN994475) | |
| FRAG1104 (Celebrity Chic UKB06022) | |
| EO806 (Organic Tea Tree Oil) | |
| EO807 (Organic Lavender Oil) | |
| EO898 (Orange Sweet Essential Oil | |
| UN1169) | |

TABLE 2

Caprilyc capric triglyceride, Stearic acid, Glyceryl Strearate, Cetearyl Alcohol, Q10, sodium Lauroyl, Glutamate, Retinol Palmitate, Cetearyl Alcohol, Shea butter, Isolanolin, Sorbitan stearate, lactate, urea, Hyluronic Acid, Saponins, D-Panthenol, Glycerin, Sodium Anisate, sodium levulinate, Glyceril Caprilate, EDTA, CaprylyL Glycol, Potassium Sorbate, Caprylic acid combo, Cetyl palmitate, Stearic acid, Cetearyl alcohol, Sodium lauroyl glutamate, Caprilyc capric triglyceride, Sorbitol, Glyceryl stearate, Demin sterile water, Disodium EDTA 0.1%, Hyluronic acid, Retinol (tretinoin) 0.5%, Saponin, Q enzyme10, Glycerrhinitic acid, Collagen, lacto ceramide, L-Cartinine, Lactic acid, Glycolic acid, Sorbitan stearate, Sorbitol, Lactate, Decandenol, Licorice extract, Green tea Extract, *Arnica*, calcium chloride, gluconate, Thrombin, Demineralised sterile water, Vitamin A, PEG-40 sterarate, Ascorbyl palmitate, Glycine Argenine HCL, Sodium hyluronate, Lauroyl Lysine

TABLE 3

1-Bladderwrack extract (seaweed): Derived from the dried thallus (bulbous root) of *Fucus vesiculosus*, a type of seaweed.
2-Horsetail extract: *Equisetum arvense*, commonly known as horsetail, mare's tail, shave grass, or bottle brush, is a plant that grows throughout central Europe.
3- *Hydrocotyl* extract: *Hydrocotyl asiatica*, commonly known as gotu kola or Indian pennywort.

The composition may comprise one or more natural ingredients listed in table 3.

TABLE 4

EDTA
Glycerin
Xanthan Gum
Avenacare Beta Glucan - Beta Glucan, Water, Maltodextrin
Collasurge - Aqua, Collagen Amino Acids, Potassium Sorbate, Ethylhexyl Glycerin, Phenoxyethanol
Crotein M - Hydrolysed Collagen
Sodium Hydroxide

TABLE 5

Figure 1:
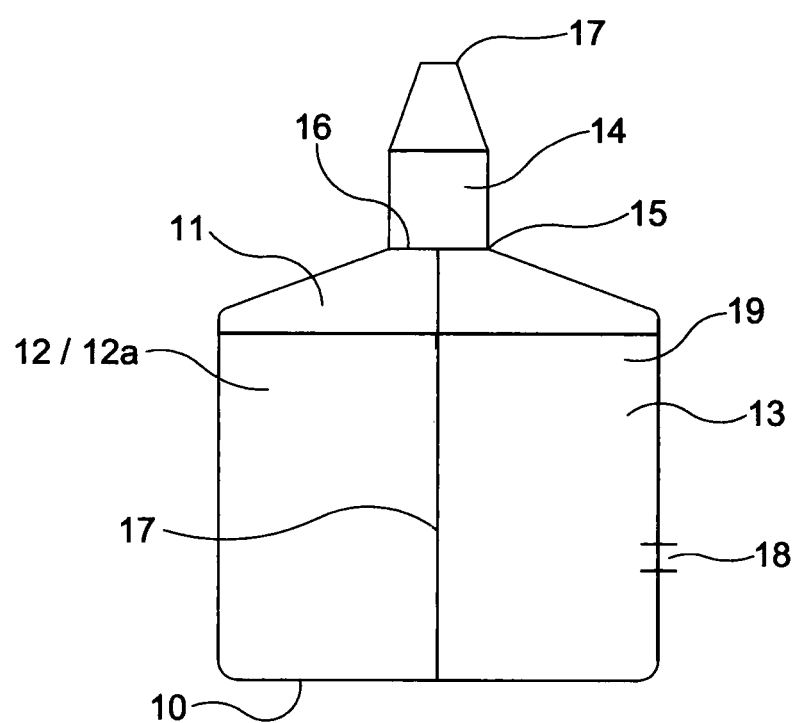
FIG. 1 shows a view of an embodiment of a container of the present invention.

Preservatives:

Dermosoft 1388 - Water, Levulinic Acid, Parfum, p-Anisic Acid, Sodium Hydroxide, Glycerin
Gerogard 221 - Benzyl alcohol, Water, Dehydroacetic Acid
Dermosoft GMCY - Glyceryl Caprylate
Potassium sorbate FIG. 1 shows a side view of an embodiment of a container according to the present invention. The container 10 may be made of any suitable material, for example rigid or flexible plastics.

Alternatively, one of the chambers, 11 may be arranged to be filled with an activator 12a according to the present invention. One of the chambers 13 may be filled with a cosmetically acceptable carrier 19 and may be arranged with an opening, valve or port 18 arranged to allow platelet rich plasma (PRP) to be introduced into the chamber so that it mixes with the cosmetically acceptable carrier. The opening, valve or port may be arranged to be re-sealable after introduction of the PRP, for example by being equipped with a lock or cap or being a rubber seal that can be injected through.

The container may further comprise a mixing chamber 14 in communication with each of the chambers 11 and 13 so arranged that contents of each of the chambers can enter the mixing chamber in a required ratio. A valve, seal, cap or lock may close an exit from the mixing chamber 17 which allows the contents of the mixing chamber to exit the container when required. The container may be activated, for example by squeezing the container or by a mechanism that urges the contents of the two chambers 11 and 13 into the mixing chamber 14 in a required ratio and the mixed contents out of the container via an exit 17. The container may be activated on multiple occasions, each activation causing a suitable portion of the contents of each of the chambers to be mixed together and to exit the container.

Figure 2:
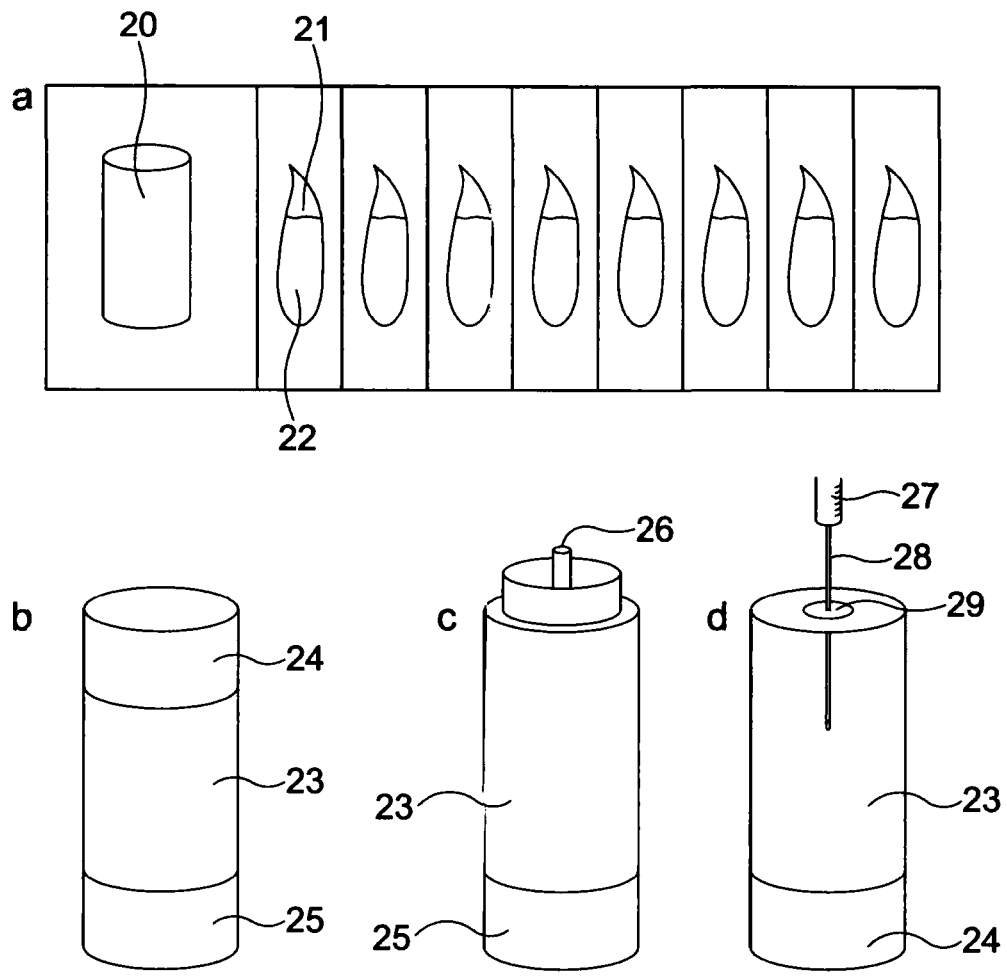
FIG. 2 shows a view of an embodiment of a container of the present invention, the whole container is shown in FIG. 2a, embodiments of a chamber suitable for containing PRP is shown in FIGS. 2b-d.
Figure 3:
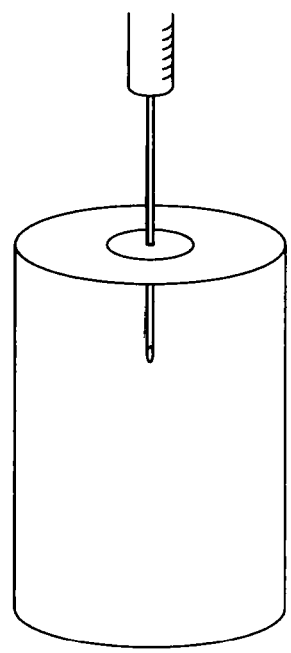
FIG. 3 shows an embodiment of a chamber suitable for containing PRP.
Figure 4A:
Figure 4A:
Figure 4A:
Figure 4A:
Figure 4B:
Figure 4B:
Figure 4B:
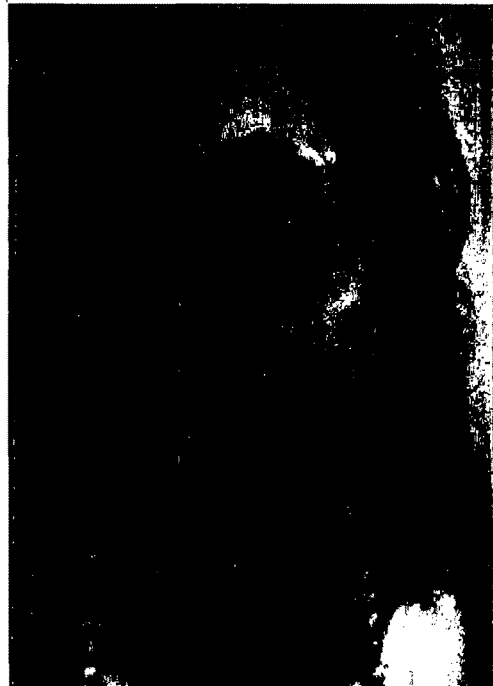
Figure 4B:
Figure 4C:
Figure 4C:
Figure 4C:
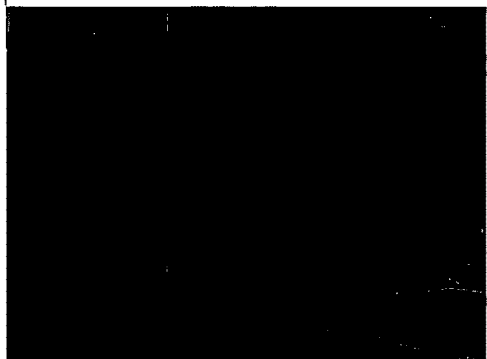
Figure 4C:
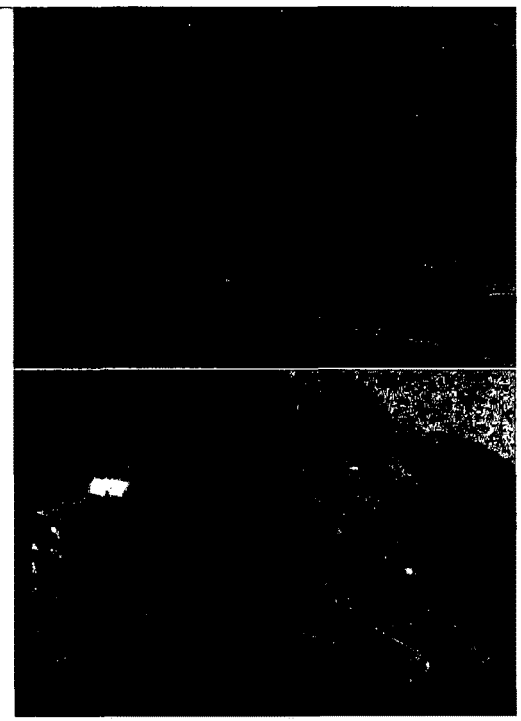
Figure 4D:
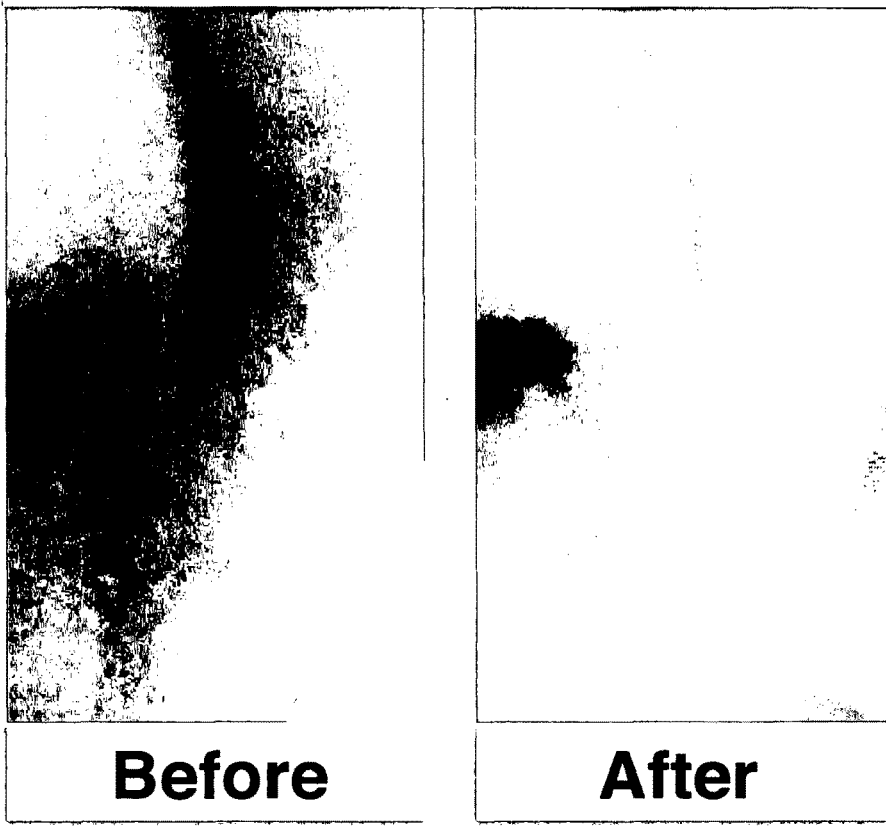

FIG. 2a shows a view of an embodiment of an embodiment of the container of the present invention. The container comprises a chamber 20 suitable for containing PRP, the container 20 may be sterile. The container comprises a multiplicity of chambers 21 comprising a cosmetically acceptable carrier 22. The cosmetically acceptable carrier may comprise an activator. The chambers comprising cosmetically acceptable carrier can be opened and a suitable amount of PRP can be added to the cosmetically acceptable carrier and mixed before applying the composition to the skin.

FIG. 2b shows a side view of a chamber suitable for containing PRP. The chamber 23 has a top lid 24 and a bottom lid 25. FIG. 2c shows the chamber 23 with the top lid removed to show that the chamber is equipped with a dropper 26 to allow drops of PRP to be shaken out of the chamber. FIG. 2d shows a view of the chamber 23 upside down with the top lid 24 in place. The bottom lid has been removed. PRP in a syringe 27 with a needle, 28 is injected through a rubber seal 29 that allows PRP to be transferred into the chamber under sterile conditions.

Tests on Human Volunteers

Platelet Rich Plasma is to be used topically, in combination with a Serum containing Collagen. The Collagen in the serum, when in contact with the PRP, induces platelet activation and release growth factors from the activated platelets.

A serum containing collagen has been prepared with the following formulation:

TABLE 6

| CAS Number | INCI | Function/Description | % |
| --- | --- | --- | --- |
| 7732-18-5 | Aqua (Water) | Solvent | 94.5895 |
| 56-81-5 | Glycerin | Humectant & Moisturiser | 2.0015 |
| 73049-73-7 | Hydrolyzed Collagen | Skin Conditioning Agent | 1.0600 |
| 26402-26-6 | Glyceryl Caprylate | Emollient, Emulsifier, Emulsifier: HLB 06 - 10.9 | 1.0000 |
| 11138-66-2 | Xanthan Gum | Emulsion Stabiliser, Skin Conditioning Agent, Surfactant, Viscosity Control | 0.9000 |
| 110-44-1 | Sorbic Acid | Antimicrobial | 0.3000 |
| 139-33-3 | Disodium EDTA | Chelating Agent | 0.1000 |
| 9050-36-6 | Maltodextrin | Absorbant &/or Abrasive Powder, Emulsion Stabiliser, Film Former &/or Hair Fixative | 0.0200 |
| 532-32-1 | Sodium Benzoate | Antimicrobial | 0.0100 |
|  | Oat Beta Glucan | Skin Conditioning | 0.0100 |
| 24634-61-5 | Potassium Sorbate | Antimicrobial, Vitamin and vitamin derivatives | 0.0060 |
| 590-00-1 |  |  |  |
| 123-76-2 | Levulinic Acid | Skin conditioning | 0.0015 |
| 19856-23-6 | Sodium Levulinate | Skin conditioning | 0.0015 |
|  |  |  | 100.0000 |

Product Specification

The Collagen Serum is a pale yellow, thin liquid with a hazy appearance.

The pH of the Collagen Serum is pH 5.20-5.50 and the Viscosity is 4000-7000 cps using Spindle 4@5.

Product stability and Preservation

The Collagen Serum remains suitably stable for the duration of a stability test, with a recommended shelf life determined to be 12 months from the date of opening.

The Collagen Serum has passed a full challenge test carried out to the European Pharmacopoeia standards.

Clinical Tests 9 subjects were recruited who wanted to improve the appearance of areas of their skin. These patients were divided into three groups.

Group 1

Blood was taken from each group 1 subject and centrifuged to separate plasma from other blood components such as red blood cells and white blood cells. Only the richest part of plasma called PRP or F2 fraction was collected as this is the fraction that is richest in platelets. The poorer fraction: PPP or F1 was not used in the serum.

PRP was injected into the skin using a series of intradermal injections across the treated area. The remaining PRP was stored. Each day for the following eight days a sample of PRP was mixed with equal volume of serum containing collagen and the mixture was applied to the treated area. On day eight further blood was taken and fresh PRP F2 was collected so that the topical treatment was continued for another 8 days after the day of injection treatment.

Group 2

Blood was taken from each group 2 subject and centrifuged to separate plasma from other blood components such as red blood cells and white blood cells. Only the richest part of the plasma, PRP fraction or F2 was separated and collected from the rest of the plasma as this is the fraction that is richest in platelets.

The PRP was stored. Each day for the following eight days a sample of PRP was mixed with equal volume of serum containing collagen and the mixture was applied to the treated area on one side of the subject's face. On day 8 and 16 further blood was taken and fresh PRP (or F2) was collected so that the topical treatment was continued for a total of 24 days after the start of treatment treatment. No PRP injections were given to this group, only topical treatment with PRP mixed with collagen serum.

Group 3

The subjects in group 2 applied the collagen serum twice a day for 24 days without any injections or any PRP mixed with the serum.

Results

The appearance of the skin on the treated area before and after the treatment for each subject is shown in FIG. 4. Pictures of the treated areas of patients 1, 2 and 3 from group 1 and patients 1, 2 and 3 from group 2 show a comparison of the skin before the treatment and after the treatment. Group 1 had PRP injections in the treated area followed by using serum mixed with PRP each day for 16 days. Group 2—only used serum mixed with PRP each day for 24 days on one side of their face so we could compare the difference with the other side of their face Group 3—used the collagen serum only (without adding PRP to it).

After using the PRP Injections for as anti aging treatment we know that PRP activates tissue regeneration and improves the tone and skin elasticity.

By:
stimulating the natural production of Hyaluronic Acid by our own cells
promoting the increased secretion of Collagen and Elastin which generates a greater consistency, firmness and reduced sagging in the skin
it improves the skin hydration
softens lines and wrinkles
it increases the luminosity and gives the skin a higher luster.

The only problem with the injections is the post operative swelling, bruising caused by many injections all over the sensitive areas like face and neck, soreness and the fact that the effect doesn't last very long which is why the present invention will dramatically improve the effect of the PRP, here dude the recovery time from the post operative problems and maintain the results for much longer.

The only problem with the injections is the post operative swelling, bruising caused by many injections all over the sensitive areas like face and neck, soreness and the fact that the effect doesn't last very long. The advantage of the present invention is that mixing PRP with serum and using it post PRP injections dramatically improves and prolongs the effect of the PRP and also allows the active factors to penetrate into the skin without the need for injection. The PRP with serum can be used as a course of treatment where a portion of PRP is mixed with a portion of serum each day to activate fresh platelets every day and the activated platelets are applied to the skin. This treatment can be carried out alone or after a course of treatment of PRP injection to prolong and enhance the effects of the PRP by injection treatment and also to help reduce the amount of bruising, swelling and soreness caused by the PRP by injection treatment.

Feed Back from the Clients in Group 1, 2 and 3

Group 1

Client 1: was a 47 years old lady who had PRP injections both in the face and hands followed by using our plasma serum for 8 days. Before the treatment she suffered from red patchy areas on her cheeks and the side of her nose as you can see in the first picture below on the left. Immediately after the PRP injections her face was slightly swollen and inflamed because of the injections. It also felt very sore. I made her the plasma serum that day and she started using it immediately and carried on for 8 days.

After 8 days the red patchy areas were all gone. The dark circles under the eyes improved. She reported that her skin felt softer, plumper and more hydrated and she had a healthy "Glow". She no longer needed to use any foundation on her skin.

The same client had her hands treated by PRP injections followed by 8 days using the plasma serum Hands Before:

Skin was very dry. Red patchy areas and deep lines around the wrist. Even using hand creams several times daily was not enough to keep the skin moisturized and soft. As a result skin looked old and wrinkly Hands after Treatment The skin was much softer, tighter and more hydrated. The redness had faded dramatically on the wrist and the deep lines had softened.

The soreness and bruising after the PRP injections healed very quickly. much quicker than it would normally The skin on the hands felt soft and was glowing. It was softer, more hydrated, lines and patchy red areas had faded dramatically Client 2: This was a 67 years old lady with deep frown lines and lots of smaller lines around the eyes, on the cheeks and the chin. She had deep dark circles below the eyes and patchy red/brown areas all over her face. To this lady sagging was the biggest problem and previous filler treatments on her face weren't giving her the result she desired.

She was treated with just PRP injections 9 months ago. She took about 5 days to recover from post-operative swelling and bruising. After that skin felt great but it didn't last very long.

This time I treated her with PRP injections first followed by using my Plasma serum for 8 days.

Not only she recovered from post-operative swelling, soreness and bruising within 24 hours, her skin continued to feel softer, plumper, and brighter and had a very healthy glow. The biggest improvement with this lady was the tightening of the skin. She described it as 'A gentle face lift'

The little lines on the cheeks and chin softened dramatically. The deep frown lines also softened. The areas under her eyes looked brighter and healthier and her skin had a more even and brighter tone.

Client 3 This was a 32 years old man with a very deep Nasio Labial fold (laughter line) which made him look older than his age. The skin inside the fold was also very dry and made shaving very hard for him.

This subject was treated with one session of deep PRP injections followed by using the Plasma serum for 8 days. The fold didn't completely disappear but improved a lot it now looks more like a fine line. The skin also felt softer, tighter and more hydrated.

Group 2:

The clients in this group reported very similar feedback: The treated side of the face felt much tighter, more hydrated, plumper and smoother than the untreated side throughout the whole 24 days despite being out in the sun and wind.

The dark circle around the eyes looked much lighter.

They all reported a new healthy "Glow"

As a result of this rehydration the lines around the eyes looked much softer.

Those who had very dry and patchy skin and after using the serum for 24 days reported softer, plumper, tighter and more even tone on the skin on the treated side while the untreated side remained the same.

Group 3:

This group reported no significant or visible improvements other than the skin felt a little more moisturized whenever they applied the collagen serum on but the effect didn't last more than 2-3 hours.

Kit

The kit may contain:

Eight plastic capsules containing the collagen serum (cosmetically acceptable carrier comprising collagen activator) for 8 days use or a suitable number of plastic capsules, one for each day or one for each application of the PRP. The amount of collagen serum in each capsule may be enough for one application. The collagen serum will be mixed with the same volume of PRP, mixed between finger tips and applied on the face, neck, chest and/or hands.

A container for holding the PRP made of a suitable material, for example Steriline polypropylene which according to the test described in this application has proven to be the best material for storage of PRP (also called F2 which is the richer part of plasma).

The PRP container may be designed to reduce the amount of air that flows into the bottle so that there is some oxygen inside but not a constant flow of oxygen. The container may be arranged to dispense the PRP in a dropwise manner so that the user can dispense a suitable number of drops of PRP to be mixed with the cosmetically acceptable carrier for each application.

3—A small battery driven vibrating table is also included now so that the client can keep the PRP agitated for the 8 days. Although our test showed great results even with the PRP group that was only shaken a few times/day we know that the best results are always achieved if the PRP is agitated constantly which is why a little vibrating table is in the kit.

Platelet Storage Conditions

Whilst PRP is generally preferred to recombinant growth factors in promotion of wound healing there is a paucity of data on stability of PRP preparations in this clinical setting. Being anucleate, platelets have a short in vivo lifespan of 8-10 days, and platelet donations taken into citrate-based anticoagulants stored at 22° C.±2° C. with continuous, gentle agitation are generally assigned a 5 day expiry. In our study we investigated serial (daily), collagen-induced PDGF-BB release from normal donor platelets stored at room temperature over 8 days under variable conditions.

Collection of Donor Platelets

A total of 125.0 mL of blood was taken from a haemostatically asymptomatic, clinically well adult male donor into 25 BD Vacutainer® tubes (Bunzl Healthcare, Enfield, UK), each containing 1.0 mL of Acid-Citrate-Dextrose solution B (ACD-B) as the anticoagulant.

The non-traumatic venepuncture was performed with minimal stasis using a 21 g-butterfly needle. The donor had not received any drugs known to affect platelet function in the preceding two weeks, or any foodstuffs known to affect platelet function in the preceding five days.

Blood for platelet diagnostics is normally taken into 0.105M tri-sodium citrate in a ratio of nine parts blood to one part anticoagulant. However, this is based on diagnostic assays being performed within four hours of venepuncture to assess function on freshly drawn platelets before natural deterioration adversely affects diagnostic accuracy. The choice of ACD-B as anticoagulant for this study was based on the work of Lei et al who demonstrated that ACD-B was superior to tri-sodium citrate in maintaining platelet structure integrity and preventing spontaneous aggregation.

Preparation of Platelet-Rich Plasma

The blood was allowed to cool for 15 minutes after the venepuncture to prevent formation of plasma clots. The tubes were then centrifuged at 22° C. in an IEC Centra CL3 centrifuge (Thermo Scientific, Basingstoke, UK) at 130 RCF (800 RPM) for 20 minutes to generate PRP.

After centrifugation, the PRP was pooled by transferring into two 30 mL Sterilin™ polypropylene universal containers (Thermo Scientific) using plastic transfer pipettes and avoiding the white blood cell-rich buffy coat layer. Use of polypropylene containers and plastic pipettes prevents platelet activation during sample manipulation. The contents of the two containers were multiply inter-mixed to achieve homogeneity.

The remaining whole blood was centrifuged at 2450 RCF (3500 RPM) for 10 minutes to obtain platelet poor plasma (PPP) for use as a blank in the collagen-induced platelet activation. The PPP was transferred into a separate universal container.

A blood count was performed on the PRP [12] using a Sysmex PocH 100i (Sysmex UK, Milton Keynes, UK) to check that:

The platelet count was between $150\text{-}600 \times 10^9/L$

The white blood cell count was $<0.5 \times 10^9/L$

The red blood cell count was $<0.5 \times 10^{12}/L$

If the platelet count is too high, artefactual inhibition of in vitro aggregation can occur, and too many red blood cells will interfere with detection of aggregation. White blood cells can inhibit platelet aggregation so it is important that most of them are removed from PRP.

Collagen-Activated Platelet Aggregometry

Immediately after preparation, aliquots of the PRP were subjected to activation by Collagen Reagent HORM® (Takeda Austria, Linz, Austria), an equine tendon collagen suspension, in a PAP8 platelet aggregometer (Alpha Laboratories, Eastleigh, UK). The PAP8 employs light transmittance aggregometry, which is summarised in FIG. 5.

The platelets were activated with collagen at a final concentration in the PRP of 5 μg/mL, a standard concentration for diagnostic purposes that should instigate full aggregation in normal platelets. Separate aliquots were activated with collagen at a concentration of 10 μg/mL to ascertain whether doubling the dose might maximise aggregation, and thus, α-granule content release. Once aggregation was complete, the aliquots were centrifuged to pellet the platelet aggregates and the supernatant removed and frozen at −80° C.
Storage of Platelet-Rich Plasma The remaining PRP was stored under different conditions in two types of container. Container 1 was a 70 mL Nunc™ non-treated flask (Thermo Fisher Scientific, Langenselbold, Germany), a sterile, non-activating polystyrene tissue culture flask, which is shown in FIG. 6(*a*). Although the polystyrene body of the flask is not oxygen permeable, the filter cap permits a constant air flow. Container 2 was a 30 mL Sterilin™ polypropylene universal container (Thermo Scientific), which is sterile but not oxygen permeable, which is shown in FIG. 6(*b*).

Each container type was used to store PRP in four different ways over an eight day period, as described below:
(a) Kept agitated throughout an 8 day storage
(b) Gently shaken/inverted several times per day
(c) Kept stationary throughout
(d) Kept agitated throughout an 8 day storage+addition of PGE1

The 150 mL volume of donated blood plus anticoagulant yielded approximately 65 mL of PRP, which permitted storage of approximately 8.0 mL of PRP in each container.

It has long been recognised that gently agitating platelets during storage reduces activation and debris formation. It has been shown that an interruption of one day has negligible, measurable effect, but longer periods can result in significant, deleterious changes. For this reason, aliquots of PRP were stored constantly agitated, intermittently agitated/mixed or kept stationary to assess the impact of variable agitation. An additional constantly agitated storage condition was introduced to include addition of prostaglandin E1 (PGE1), a natural platelet inhibitor that triggers an increase in cyclic adenosine monophosphate levels which counteracts platelet activation by reducing calcium flux. Addition of PGE1 to PRP reduces platelet activation during storage whilst permitting a response to most agonists during in vitro analysis. PGE1 was added to the PRP at a final concentration of 10 μg/mL, the standard concentration for diagnostic use. All PRP was stored at room temperature since cold storage activates platelets.

A Luckham R100 Rotatest Shaker (FIG. 7) was used to agitate the containers requiring constant agitation. The platform was rotated on setting 5, a mid-point setting to approximately mimic that employed for platelets being stored for transfusion. The aliquots being mixed intermittently were shaken/inverted hourly during the laboratory core hours of 09.00-17.00 h for the first five days and left undisturbed for days six and seven as they were over a weekend.
Serial Collagen-Activated Platelet Aggregometry At approximately the same time each day as when the freshly prepared PRP was analysed, aliquots of mixed PRP from each of the eight containers were separately activated in the PAP8 aggregometer with collagen at a final concentration in PRP of 10 μg/mL and the aggregation patterns recorded. Once aggregation was complete, the aliquots were centrifuged to pellet the platelet aggregates and the supernatants removed and frozen at −80° C. This was undertaken on days 2-5 and day 8. Platelet counts were also performed each day as an on-going assessment of PRP quality and platelet activation and spontaneous aggregation. Platelet counts were performed immediately prior to aggregometry.

Analysis of Supernatants for PDGF-BB

To assess storage and release of growth factors from stored platelets, measurement of PDGF-BB was chosen as a representative marker since it has been employed in similar studies for the same purpose, becaplermin is a recombinant version of PDGF-BB, and reagents for analysing PDGF-BB levels are commercially available.

PDGF-BB levels in the supernatants were quantified with Human PDGF-BB Platinum ELISA reagent kit (Affymetrix eBioscience, Hatfield, UK). The principle of measurement of PDGF-BB by enzyme-linked immunosorbent assay (ELISA) is depicted in FIG. 8.

Prior to use in quantification of released PDGF-BB in the stored supernatants, the kit was evaluated for standard curve linearity and analytical precision. Whilst each step of the assay was performed manually, end-point detection, standard curve generation, test raw data and calculation of final results were all performed on a Dynex DS2™ ELISA analyser (Instrumentation Laboratory, Warrington, UK).
Cell Counting of PRP on the Day of Donation The blood cell counts on the PRP immediately after harvesting, and prior to collagen-induced platelet aggregation, are shown in Table 1.

TABLE 7

| Cell counts on PRP Parameter | | |
| --- | --- | --- |
| | Results | Units |
| White cell count | 0.0 | ×109/L |
| Red cell count | 0.00 | ×1012/L |
| Platelet count | 236 | ×109/L |

The aliquots activated with 5 μg/mL collagen achieved 93% and 85% aggregation (mean 89%). The aliquots activated with 10 μg/mL collagen achieved 91% and 84% aggregation (mean 88%). Although this revealed no increase in the activation/aggregation responses to a doubling of the standard collagen concentration, the 10 μg/mL collagen concentration was adopted for the serial testing to allow for ageing of the platelets during the course of the experiments.
Collagen-Induced Aggregation of Stored PRP: Day 2

Collagen-induced aggregometry was performed in duplicate on aliquots of PRP from each storage situation. The aggregation traces for PRP stored in the Nunc™ flasks are shown in FIG. 10, and the non-oxygen permeable universal containers in FIG. 11. Platelet count (Plt) prior to aggregometry and mean percentage final aggregation (MA) for each duplicate are given in the legends.
Collagen-Induced Aggregation of Stored PRP: Day 3

Collagen-induced aggregometry was performed in duplicate on aliquots of PRP from each storage situation. The aggregation traces for PRP stored in the Nunc™ flasks are shown in FIG. 12, and the non-oxygen permeable universal containers in FIG. 13. Platelet count (Plt) prior to aggregometry and mean percentage final aggregation (MA) for each duplicate are given in the legends
Collagen-Induced Aggregation of Stored PRP: Day 4

Collagen-induced aggregometry was performed in duplicate on aliquots of PRP from each storage situation. The aggregation traces for PRP stored in the Nunc™ flasks are shown in FIG. 14, and the non-oxygen permeable universal containers in FIG. 15 Platelet count (Plt) prior to aggregometry and mean percentage final aggregation (MA) for each duplicate are given in the legends.

Collagen-Induced Aggregation of Stored PRP: Day 8

Collagen-induced aggregometry was performed in duplicate on aliquots of PRP from each storage situation. The aggregation traces for PRP stored in the Nunc™ flasks are shown in FIG. 18, and the non-oxygen permeable universal containers in FIG. 19 Platelet count (Plt) prior to aggregometry and mean percentage final aggregation (MA) for each duplicate are given in the legends.

Plots of changes in % aggregation over time in variably stored PRP are shown in FIGS. 20-23.

Platelet Parameters Over Time in Variably Stored PRP

In addition to counting platelet numbers, the Sysmex PocH 100i analyser generates other platelet diagnostic parameters, as described below:

Mean platelet volume (MPV)

Platelet distribution width (PDW) calculates the relative width of platelet volume distribution Platelet-large cell ratio (P-LCR) is the ratio of platelets smaller than 12 fL to those with a volume between 12-30 fL Reference ranges from literature for whole blood are as follows:

MPV: 7.5-11.5 fL
PDW: 9.3-16.0 fL
P-LCR: 24.8-41.2%

Table 8 shows the platelet parameters in variably stored PRP immediately prior to collagen activation on each day.

TABLE 8

Serial platelet parameters in variably stored PRP

| Storage container | Storage conditions | Platelet parameters | Day 1 | Day 2 | Day 3 | Day 4 | Day 5 | Day 6 |
|---|---|---|---|---|---|---|---|---|
| No storage | Fresh PRP | PDW (fL) | 11.6 | — | — | — | — | — |
| | | MPV (fL) | 9.7 | | | | | |
| | | P-LCR (%) | 22.3 | | | | | |
| Nunc ™ flask | Constant agitation | PDW (fL) | — | 16.2 | 15.2 | 14.0 | 12.2 | 8.8 |
| | | MPV (fL) | | 11.8 | 11.1 | 10.7 | 10.1 | 8.6 |
| | | P-LCR (%) | | 41.2 | 36.0 | 33.0 | 28.5 | 18.4 |
| | Intermittent agitation | PDW (fL) | — | 13.4 | 17.5 | 14.4 | 14.2 | 12.1 |
| | | MPV (fL) | | 10.7 | 11.8 | 11.3 | 11.0 | 10.4 |
| | | P-LCR (%) | | 29.7 | 41.8 | 36.4 | 34.7 | 30.5 |
| | Stationary | PDW (fL) | — | 12.5 | 16.4 | 16.1 | 15.2 | 13.9 |
| | | MPV (fL) | | 10.2 | 11.7 | 11.7 | 11.4 | 11.0 |
| | | P-LCR (%) | | 26.4 | 41.5 | 41.2 | 38.0 | 35.6 |
| | Constant agitation + $PGE_1$ | PDW (fL) | — | 16.5 | 15.2 | 14.1 | 12.2 | 9.7 |
| | | MPV (fL) | | 11.7 | 11.1 | 10.9 | 10.2 | 8.9 |
| | | P-LCR (%) | | 41.3 | 36.4 | 34.4 | 29.1 | 20.2 |
| Universal | Constant agitation | PDW (fL) | — | 9.9 | 9.4 | No | 8.6 | 8.3 |
| | | MPV (fL) | | 8.8 | 8.6 | analysis | 8.6 | 8.4 |
| | | P-LCR (%) | | 16.9 | 17.9 | output | 19.2 | 18.3 |
| | Intermittent agitation | PDW (fL) | — | 11.3 | 11.6 | 12.6 | 12.0 | 13.8 |
| | | MPV (fL) | | 9.6 | 9.7 | 10.2 | 10.1 | 10.7 |
| | | P-LCR (%) | | 21.0 | 21.9 | 25.3 | 24.9 | 31.1 |
| | Stationary | PDW (fL) | — | 11.0 | 11.8 | 11.5 | 12.3 | 14.4 |
| | | MPV (fL) | | 9.5 | 10.1 | 10.1 | 10.1 | 11.4 |
| | | P-LCR (%) | | 19.6 | 23.8 | 23.8 | 23.5 | 36.6 |
| | Constant agitation + $PGE_1$ | PDW (fL) | — | 9.8 | 8.7 | 8.5 | 7.8 | 8.9 |
| | | MPV (fL) | | 8.8 | 8.3 | 8.1 | 8.1 | 8.6 |
| | | P-LCR (%) | | 16.4 | 17.1 | 13.8 | 15.4 | 20.2 |

TABLE 9

Serial PDGF-BB levels in variably stored collagen (10 µg/ml) activated platelets

| Storage container | Storage conditions | PDGF-BB (pg/mL) | | | | | |
|---|---|---|---|---|---|---|---|
| | | Day 1 | Day 2 | Day 3 | Day 4 | Day 5 | Day 6 |
| No storage | Fresh PRP | 18 734 | — | — | — | — | — |
| Nunc ™ flask | Constant agitation | — | 13 190 | 14 580 | 11 081 | 13 689 | 10 332 |
| | Intermittent agitation | — | 12 871 | 11 488 | 10 589 | 9 991 | 10 042 |
| | Stationary | — | 11 159 | 12 441 | 10 973 | 11 969 | 11 210 |
| | Constant agitation + $PGE_1$ | — | Not available | 10 055 | 7 842 | 9 796 | 9 808 |
| Universal | Constant agitation | — | Not available | 12 486 | 12 905 | 10 950 | 9 925 |
| | Intermittent agitation | — | 15 303 | 14 141 | 12 514 | 10 547 | 8 701 |
| | Stationary | — | 10 875 | 13 649 | 12 939 | 10 938 | 11 398 |
| | Constant agitation + $PGE_1$ | — | 13 082 | 11 836 | 9 829 | 10 148 | 8 967 |

Note that results for Day 2 of constant agitation + $PGE_1$ in the Nunc ™ flask and constant agitation in the universal are unavailable due to technical problems Virtually without exception, publications on the use of Plasma for cosmetic and wound healing uses describe use of freshly drawn PRP, or in some cases, PRP that has been frozen and thawed. The aim of the present study was to evaluate growth factor release from PRP stored at room temperature over a number of days, using PDGF-BB as the marker. Freezing PRP is known to damage the platelets causing a rapid release of growth factors on thawing. For this reason frozen PRP may not be useful for techniques where the plasma is stored for use on several consecutive days unless the PRP is frozen in portions so that one may be thawed immediately before each application.

Effects of Storage on Platelet Number and Size Parameters

There was a steady fall in platelet count over time in all storage containers and conditions except for the two universals under constant agitation which exhibited a marked fall on Day 2 before beginning a steady decline after that. There is no immediately obvious explanation for this observation, although the platelet parameter results are revealing. Both these containers had lower PDW, MPV and P-LCR values than the stationary and intermittently agitated universals on all days of analysis. The smaller platelet size, narrower width distribution and lower ratio suggest that larger platelets were missing from these two containers, but why this may be the case is unclear. It would be tempting to suggest that the intensity of agitation was too high and had achieved a degree of activation, with the more reactive larger platelets perhaps being more susceptible, yet this was not mirrored in the two constantly agitated Nunc™ flasks with apparently greater oxygen access. The otherwise steady decline in platelet count in all containers will have been largely due to the well described platelet storage lesion.

Remarkably, all PDW, MPV and P-LCR results from universal-stored PRP were lower than their Nunc™ flask-stored counterparts, indicating container-induced effects. Furthermore, platelet parameters on Day 2 were closer to those of fresh PRP in the universal-stored PRP than Nunc™ flask-stored PRP. Minor increases in MPV and PDW during storage up to five days have been reported previously but not to the marked extent of the PDW results in the Nunc™ flask-stored PRP. If MPV does not normally increase significantly over this time in stored PRP, the moderate increase on Day 2 in these flasks accompanied by marked increase in PDW, particularly in the constantly agitated flasks, is suggestive that a degree of microaggregate formation had occurred. This would explain the increase in P-LCR that was suggesting the presence of higher numbers of larger cells, which were more likely to have been microaggregates. The only moderately increased MPVs indicate they remained small enough for the vast majority to be counted as platelets. Interestingly, PDW, MPV and P-LCR reduced over time in the constantly agitated Nunc™ flasks, probably due to increasing spontaneous aggregation over time such that the largest aggregates were not aspirated into the blood count analyser. Further evidence of microaggregate formation was found from apparent low red blood cell counts in many of the Nunc™ flask-stored PRP results (data not shown). There were no red cells in the PRP on Day 1 and these counts were due to small populations of aggregates too large to be counted as platelets. The only universal-stored PRP to register a low red cell count was from the stationary universal on Day 8, which had the highest PDW, MPV and P-LCR values of any universal-stored PRP. MPV was more stable over time in the intermittently agitated and stationary Nunc™ flasks, suggesting that constant agitation exacerbated spontaneous aggregate formation in a storage situation where low-level activation was already more likely. There was little difference between the platelet parameters of the constantly agitated Nunc™ flasks with and without PGE1, or the universals, so it appears that the PGE1 did not suppress spontaneous aggregation. It may be that a higher concentration was required, or that the PGE1 is insufficiently stable for stored PRP.

Converse results were seen in universal-stored PRP in that PDW, MPV and P-LCR were lower in the constantly agitated universals than in the intermittently agitated and stationary universals. As described above, there was a curious fall in platelet count, PDW, MPV and P-LCR parameters on Day 2 in the constantly agitated universals, which may have been due to an immediate, more intense formation of aggregates that were not counted in the analyser, followed by relatively small reductions in PDW and MPV over time. In contrast to the steep falls in P-LCR over time in the constantly agitated Nunc™ flasks, the counterpart universals exhibited mild increase over time, suggesting low level aggregate formation. Some degree of activation and aggregate formation is expected in stored platelets. Only the intermittently agitated and stationary universals mirrored baseline PDW, MPV and P-LCR values on Day 2, with the anticipated gradual but small increases over time of PDW and MPV. The increases in P-LCR over time were more marked, suggesting a degree of aggregate formation in these containers too.

Based on these observations, the intermittently agitated universal maintained the greater platelet integrity over time. Hunter et al showed that interruption of agitation for one day produces no measurable platelet damage, so the intermittent agitation during laboratory core hours and less than 24 hour interruption overnight appears to have been sufficient to maintain comparable integrity.

Effects of Storage on Platelet Aggregation Responses

As previously reported, there was an overall continuous fall in platelet aggregability over time under all storage conditions in the study. An unanticipated finding was the remarkable fall in final percentage aggregation of Nunc™ flask-stored PRP on Day 2 and thereafter, in stark contrast to the more gradual declines in universal-stored PRP. The minimal platelet count reductions, other than from the constantly agitated universals on Day 2, indicate that relatively few platelets had formed aggregates and that the aggregation responses were a result of activation of the majority of the stored platelets. In which case, the storage conditions in the Nunc™ flasks were detrimental to overall platelet function.

Polypropylene is the preferred material for platelet storage although platelet adhesion to untreated polystyrene is normally minimal with non-activated platelets. However, binding of plasma proteins such as fibrinogen and VWF to the polystyrene can promote platelet adhesion and subsequent activation. Again, the minimal fall in platelet counts suggest this either did not occur, or occurred only minimally. Thus, the container itself would not be expected to inhibit platelet function and conditions in the PRP itself were the more likely culprit. The most probable explanation for such marked storage-induced differences in initially identical samples of PRP is a drift in plasma pH. Watts et al showed that PRP stored in a closed system to maintain pH better preserved platelet function than PRP stored in a controlled $CO^2$/air environment, which was probably related to the presence of an air/liquid interface in the latter. The universals have screw top lids which were only removed once a day to extract PRP for aggregometry, whilst the Nunc™ flasks permitted air flow. Since the 30 mL universals were used to store only approximately 8.0 mL of PRP, they likely retained sufficient oxygen in the 'dead space' until the next opening to not significantly impair platelet integrity. The anticoagulant used for sample collection can also affect pH of PRP.

A commonality in aggregometry responses between the two storage containers is the reduced final percentage aggregation in PRP from the constantly agitated samples compared to those intermittently agitated or kept stationary. This is counter-intuitive as accepted dogma is that stored platelets should be constantly, gently agitated to reduce activation and debris formation. It may be that the agitation was too harsh or too gentle for the PRP volumes and containers that were employed, or that pH changes were exaggerated by the constant movement, even in the universals since they retained an appreciable amount of air.

Effects of Storage on PDGF-BB Levels

The amount of released PDGF-BB in freshly prepared PRP is affected by numerous variables, including anticoagulant, donor whole blood platelet count, PRP preparation conditions, platelet count in PRP and type and concentration of agonist used to induce release. Nonetheless, the PDGF-BB level of 18 734 pg/mL in the freshly prepared PRP in this study broadly mapped to levels reported by other workers. From similar centrifugation conditions, Gonzalez et al reported a PDGF-BB range of 9.6-14.6 ng/mL from PRP obtained from 32 donors, and Castillo et al reported 13.0-33.2 ng/mL from five donors.

A marked fall in PDGF-BB levels was observed on Day 2 in all storage conditions where results were available. The mean percentage reduction was 32%, ranging from the 18% reduction in the intermittently agitated universal to the 42% reduction in the stationary universal. Most were followed by a steady, continuous decrease in PDGF-BB levels, some ostensibly reaching a plateau by Days 5 and 8. To a large extent these findings are unsurprising as platelet secretory capacity falls during storage, yet by Day 8, appreciable levels of PDGF-BB remained despite the expectation that the majority of platelets would be dead or poorly functional by that time. A potential explanation is that the PDGF-BB in the supernatant may have merely leaked from the platelets as they aged and membrane integrity was lost. In view of the minimal reduction in platelet counts for most storage conditions, and even the steady fall after the initial marked reduction in the constantly agitated universals, this would seem unlikely to be the only causative factor. Furthermore, if the platelets were fragmenting over time there would likely have been gradual reductions in MPV, which was only observed in constantly agitated Nunc™ flasks, whilst others remained stable or increased over time. However, microaggregate formation could mask more subtle volume loss from membrane fragmentation. If those MPV reductions in the constantly agitated Nunc™ flasks were due to fragmentation, a concomitant increase in PDW over time would be expected, but the converse was the case.

What is also interesting is that the relatively poor aggregation responses from Day 2 onwards in constantly agitated Nunc™ flask-stored PRP are not accompanied by similarly marked PDGF-BB reductions. This was true, albeit to a lesser extent, with the other paired storage conditions. It appears that some of the PDGF-BB in the supernatants is not derived from platelet release, and the explanation for this comes from other studies that additionally measured PDGF-BB in PPP. Gonzalez et al reported a range in PPP of 8.8-12.6 ng/mL, whilst Valeri et al reported a range of 1549-2813 pg/mL. There are clear between-study differences yet plasma PDGF-BB does contribute to values measured in platelet releasates unless platelets are washed prior to analysis. The mechanical trauma of PPP and PRP preparation will also have contributed to the presence of free PDGF-BB in the PPP. The platelet counts in the PRP of the study by Gonzalez et al were adjusted to 250×109/L, similar to the count in the donor PRP for this study, whilst the mean count in PRPs from the study by Castillo et al was 566× 109/L. From a clinical perspective, the PDGF-BB values from collagen-activated PRP reported in this study relate to a lower platelet count than would be used in clinical practice, so the differentiation between release from fresh and stored PRP would be greater. Again, the aim of the study was to investigate relative loss of PDGF-BB release, which had to be performed at lower platelet counts to maximise application of available analytical techniques.

Parameter Stability

Platelet rich plasma stored in the intermittently agitated universal maintained better stability in the parameters studied than that stored in other conditions. Up to Day 5 there was minimal reduction in platelet count and elevations in PDW, MPV and P-LCR, particularly in comparison with some of the marked platelet parameter changes in PRP stored in Nunc™ flasks. The platelet changes in the stationary universal were greater except the platelet count, and there is no clear explanation for the marked fall in platelet count on Day 2 in the two constantly agitated universals.

Platelet aggregation responses to collagen activation were lower in Nunc™ flask-stored PRP than universal stored PRP for the reasons described above. Higher final percentage aggregation over time was achieved by the PRP in intermittently agitated and stationary universals compared to their constantly agitated partners, other than an apparent surge on Days 5 and 8 in the universal without PGE1. However, the falls in aggregation (representing overall platelet reactivity), particularly in Nunc™ flask-stored PRP, were not accompanied by similarly dramatic reductions in supernatant PDGF-BB levels. It seems likely that although secretory capacity reduced over time, PDGF-BB levels did not fall to near zero due to a mixture of leakage from senescing platelets, mechanical trauma and innate plasma levels.

Although PRP stored in the intermittently agitated universal maintained better overall stability, it did in fact generate the lowest PDGF-BB value on Day 8 despite achieving 39% final aggregation. An important consideration is that the study merely assessed PDGF-BB concentration but not function, so it is impossible to know what levels of PDGF-BB are therapeutically efficacious, and therefore, at what point during storage the PRP should be discarded. Furthermore, the PDGF-BB itself may lose functionality over time and be therapeutically ineffective despite an apparently high level of release.

Consideration of function aside, PDGF-BB levels from activation of PRP under all storage conditions were within the range reported by Gonzalez et al for fresh PRP with a similar platelet count, up to Day 5. Although this may be encouraging in terms of storage potential, all the values were markedly lower than for fresh PRP. Without knowledge of PDGF-BB functionality, or that of other released growth factors, it would seem that freezing either the fresh PRP or the post-activation supernatant might generate a more efficacious therapeutic product. Whilst acknowledging the controversy regarding PRP cryopreservation, Roffi et al showed that frozen-thawed PRP without prior agonist activation achieved comparable in vitro effects on cultured cells to those of fresh PRP despite reductions in PDGF-AB/BB levels. The freeze/thaw cycle acts as a surrogate 'activator' by disrupting platelet membranes and inducing content release. In view of the lower growth factor levels in the freeze/thawed PRP, it may be a less efficient approach to increasing growth factor availability than agonist-induced platelet activation since they are 'packaged' within α-granules rather than free in the cytoplasm. Durante et al reported PDGF-BB levels in fresh PRP of 17 904±1346 pg/mL but reduced levels even after three freeze/thaw cycles. This suggests that freezing the post-collagen activation supernatant is more likely to generate and preserve higher growth factor levels, with the possible additional value of excluding platelet debris from the final product.

The invention claimed is:

1. A kit, comprising:
   a container for storing platelet-rich plasma (PRP); and separately
   a plurality of capsules each containing a cosmetically acceptable carrier comprising an activator, wherein the activator is collagen and the amount of cosmetically acceptable carrier in each capsule is enough for one application; and an agitation device.

2. The kit of claim 1, wherein the cosmetically acceptable carrier is arranged to be mixed with PRP.

3. The kit of claim 1, wherein the PRP container is made of polypropylene.

4. The kit of claim 1, wherein the agitation device is a battery driven vibrating table of suitable size to carry the PRP container.

5. The kit of claim 1, wherein the container is oxygen permeable such that it allows oxygen penetration into the container.

6. The kit of claim 1, wherein the agitation device is configured to agitate the PRP prior to contact with the cosmetically acceptable carrier.

* * * * *